US008334428B2

(12) United States Patent
Gelvin et al.

(10) Patent No.: US 8,334,428 B2
(45) Date of Patent: Dec. 18, 2012

(54) BACKBONE-FREE LOW TRANSGENE COPY TRANSGENIC PLANTS

(75) Inventors: Stanton B. Gelvin, West Lafayette, IN (US); Heiko Oltmanns, Dossenheim (DE); Lan Ying Lee, West Lafayette, IN (US); Bronwyn Frame, Ames, IA (US); Kan Wang, Ames, IA (US)

(73) Assignees: Purdue Research Foundation, West Lafayette, IN (US); Iowa State University Research Foundation, Inc., Ames, IA (US)

( * ) Notice: Subject to any disclaimer, the term of this patent is extended or adjusted under 35 U.S.C. 154(b) by 529 days.

(21) Appl. No.: 12/514,180

(22) PCT Filed: Nov. 14, 2007

(86) PCT No.: PCT/US2007/084668
§ 371 (c)(1),
(2), (4) Date: Aug. 19, 2009

(87) PCT Pub. No.: WO2008/085605
PCT Pub. Date: Jul. 17, 2008

(65) Prior Publication Data
US 2010/0005547 A1    Jan. 7, 2010

Related U.S. Application Data

(60) Provisional application No. 60/866,006, filed on Nov. 15, 2006.

(51) Int. Cl.
*C12N 15/84* (2006.01)
*C12N 15/10* (2006.01)
*C12N 15/90* (2006.01)
*C12N 1/21* (2006.01)

(52) U.S. Cl. ...... 800/294; 800/320; 435/6.1; 435/252.2; 435/252.3; 435/463; 435/469

(58) Field of Classification Search .................. None
See application file for complete search history.

(56) References Cited

U.S. PATENT DOCUMENTS
2007/0074314 A1   3/2007   Ye et al.

OTHER PUBLICATIONS

Oltmanns et al. Plant Physiology 152: 1158-1166 (Mar. 2010).*
Armstrong et al., Development and availability of germplasm with high Type II culture formation response, *Maize Genet. Coop Newsletter*, 65: 92-93 (1991).
Arumuganathan et al., "Nuclear DNA content of some important plant species," *Plant Mol. Biol. Rep.*, 9:208-218 (1991).
Bechtold et al., "In planta Agrobacterium mediated gene transfer by infiltration of adult Arabidopsis thaliana plants," *C. R. Acad. Sci. Paris Life Sci.*, 316:1194-1199 (1993).
Chen et al., "Characterization of the supervirulent virG gene of the Agrobacterium tumefaciens plasmid pTiBo542," *Mol. Gen. Genet.*, 230:302-309 (1991).
Depicker et al., "Frequencies of simultaneous transformation with different T-DNAs and their relevance to the Agrobacterium/plant cell interaction," *Mol. Gen. Genet.*, 201:477-484 (1985).
Deroles et al., "Analysis of the T-DNA structure in a large number of transgenic petunias generated by Agrobacterium-mediated transformation," *Plant Mol. Biol.*, 11:365-377 (1988).
Durrenberger et al., "Covalently bound VirD2 protein of Agrobacterium tumefaciens protects the T-DNA from exonucleolytic degradation," *Proc. Natl. Acad. Sci. USA*, 86:9154-9158 (1989).
Feldmann, "T-DNA insertion mutagenesis in Arabidopsis: Mutational spectrum," *Plant J.*, 1:71-82 (1991).
Francis et al., "Identification of Arabidopsis thaliana transformants without selection reveals a high occurrence of silenced T-DNA integrations," *Plant J.*, 3:464-477 (2005).
Grevelding et al., "Single-copy T-DNA insertions in Arabidopsis are the predominant form of integration in root-derived transgenics, whereas multiple insertions are found in leaf discs." *Plant Mol. Biol.*, 23:847-860 (1993).
Hiei et al., "Efficient transformation of rice (Oryza sativa L.) mediated by Agrobacterium and sequence analysis of the boundaries of the T-DNA," *Plant J.*, 6:271-282 (1994).
Hoekema et al., "A binary plant vector strategy based on separation of vir and T-region of the Agrobacterium tumefaciens Ti-plasmid," *Nature*, 303:179-180 (1983).
Hood et al., "Virulence of Agrobacterium tumefaciens strain A281 on legumes," *Plant Physiol.*, 83:529-534 (1987).
Jeon et al., "T-DNA insertional mutagenesis for functional genomics in rice," *Plant J.*, 22:561-570 (2000).
Jorgensen, et al., "T-DNA is organized predominantly in inverted repeat structures in plants transformed with Agrobacterium tumefaciens C58 derivatives," *Mol. Gen. Genet.*, 207:471-477 (1987).
Jorgensen et al., "Chalcone synthase cosuppression phenotypes in petunia flowers: comparison of sense vs. antisense constructs and single-copy vs. complex T-DNA sequences," *Plant Mol. Biol.*, 31:957-973 (1996).
Koncz et al., "The promoter of TL-DNA gene 5 controls the tissue-specific expression of chimaeric genes carried by a novel type of Agrobacterium binary vector," *Mol. Gen. Genet.*, 204:383-396 (1986).
Lichtenstein et al., "DNA cloning: A practical approach," In *Genetic Engineering of Plants*, vol. 2 (Glover, D.M., ed.). Washington, DC: IRL Press, pp. 67-119 (1986).
Nagel et al., "Electroporation of binary Ti plasmid vector into Agrobacterium tumefaciens and Agrobacterium rhizogenes," *FEMS Microbiol. Lett.*, 67:325-328 (1990).
Oltmanns et al., "Effect of Agrobacterium strain and binary vector replication origin on Agrobacterium-mediated transformation frequency and transgene copy number," Poster and Oral Presentation, *26th Annual Crown Gall Meeting* (2005) (Abstract), p. 40.

(Continued)

*Primary Examiner* — David T Fox
(74) *Attorney, Agent, or Firm* — Barnes & Thornburg LLP; Alice O. Martin

(57) ABSTRACT

Methods and compositions reduce copy number of transgenes and minimizing vector backbone sequences in plant transformation. *Agrobacterium* strains with T-DNA integrated into the chromosomal DNA of the *Agrobacterium* reduce the copy number and vector backbone sequences. Chromosomal integration vectors to integrate T-DNA into a specific locus of *Agrobacterium* chromosome are disclosed.

9 Claims, 16 Drawing Sheets

OTHER PUBLICATIONS

Ramanathan et al. "Transfer of non-T-DNA portions of the *Agrobacterium tumefaciens* Ti plasmid pTiA6 from the left terminus of TL-DNA," *Plant Mol. Biol.*, 28:1149-1154 (1995).

Stam et al., "Post-transcriptional silencing of chalcone synthase in *Petunia* by inverted transgene repeats," *Plant J.*, 12:63-82 (1997).

Wenck et al., "Frequent collinear long transfer of DNA inclusive of the whole binary vector during *Agrobacterium*-mediated transformation," *Plant Mol. Biol.*, 34:913 922 (1997).

Alonso et al., "Genome-Wide Insertional Mutagenesis of *Arabidopsis thaliana*," *Science*, 301: 653-657 (2003).

Barakat et al., "The distribution of T-DNA in the genomes of transgenic *Arabidopsis* and rice," *FEBS Letters*, 471: 161-164 (2000).

Bevan, "Binary *Agrobacterium* vectors for plant transformation," *Nucleic Acids Research*, 12 (22): 8711-8721 (1984).

Chilton et al., "Stable Incorporation of Plasmid DNA into Higher Plant Cells: The Molecular Basis of Crown Gall Tumorigenesis," *Cell*, 11: 263-271 (1977).

Close et al., "Design and Development of Amplifiable Broad-Host-Range Cloning Vectors: Analysis of the vir Region of *Agrobacterium tumefaciens* Plasmid pTiC58," *Plasmid*, 12: 111-118 (1984).

Clough et al., "Floral dip: a simplified method for *Agrobacterium*-mediated transformation of *Arabidopsis thaliana*," *The Plant Journal*, 16 (6): 735-743 (1998).

De Block et al., "Engineering herbicide resistance in plants by expression of a detoxifying enzyme," *The EMBO Journal*, 6 (9): 2513-2518 (1987).

De Buck et al., "T-DNA vector backbone sequences are frequently integrated into the genome of transgenic plants obtained by *Agrobacterium*-mediated transformation," *Molecular Breeding*, 6: 459-468 (2000).

de Framond et al., "Mini-Ti: A New Vector Strategy for Plant Genetic Engineering," *Biotechnology*, 5: 262-269 (1983).

Frame et al., "*Agrobacterium tumefaciens*—Mediated Transformation of Maize Embryos Using a Standard Binary Vector System," *Plant Physiology*, 129: 13-22 (2002).

Galbiati et al., "Large-scale T-DNA mutagenesis in *Arabidopsis* for functional genomic analysis," *Funct. Integr. Genomics*, 1: 25-34 (2000).

Gelvin, "*Agrobacterium*-Mediated Plant Transformation: the Biology behind the "Gene-Jockeying" Tool," *Microbiology and Molecular Biology Reviews*, 67 (1): 16-37 (2003).

Hamilton et al., "Stable transfer of intact high molecular weight DNA into plant chromosomes," *Proc. Natl. Acad. Sci. USA*, 93: 9975-9979 (1996).

Hanson et al., "A simple method to enrich an *Agrobacterium*-transformed population for plants containing only T-DNA sequences," *The Plant Journal*, 19 (6): 727-734 (1999).

Hirsch et al., "A Physical Map of pPH1J1 and pJB4JI," *Plasmid*, 12: 139-141 (1984).

Jeon et al., "T-DNA insertional mutagenesis for functional genomics in rice," *The Plant Journal*, 22 (6): 561-570 (2000).

Jouanin et al., "Restriction Maps and Homologies of the Three Plasmids of *Agrobacterium rhizogenes* Strain A4," *Plasmid*, 16: 124-134 (1986).

Knauf et al., "Wide Host Range Cloning Vectors: A Cosmid Clone Bank of an *Agrobacterium* Ti Plasmid," *Plasmid*, 8: 45-54 (1982).

Kohli et al., "Transgene expression in rice engineered through particle bombardment: molecular factors controlling stable expression and transgene silencing," *Planta*, 208: 88-97 (1999).

Kohli et al., "Transgene integration, organization and interaction in plants," *Plant Molecular Biology*, 52: 247-258 (2003).

Martineau et al., "On Defining T-DNA," *The Plant Cell*, 6: 1032-1033 (1994).

McElver et al., "Insertional Mutagenesis of Genes Required for Seed Development in *Arabidopsis thaliana*," *Genetics*, 159: 1751-1763 (2001).

Murray et al., "Rapid isolation of high molecular weight plant DNA," *Nucleic Acids Research*, 8 (19): 4321-4325 (1980).

Ooms et al., "Crown gall plant tumors of abnormal morphology, induced by *Agrobacterium tumefaciens* carrying mutated octopine Ti plasmids; analysis of T-DNA functions," *Gene*, 14: 33-50 (1981).

Rong et al., "picA, a Novel Plant-Inducible Locus on the *Agrobacterium tumefaciens* Chromosome," *Journal of Bacteriology*, 172 (10): 5828-5836 (1990).

Rong et al., "Genetic and Molecular Analyses of picA, a Plant-Inducible Locus on the *Agrobacterium tumefaciens* Chromosome," *Journal of Bacteriology*, 173 (16): 5110-5120 (1991).

Rossi et al., "Integration of complete transferred DNA units is dependent on the activity of virulence E2 protein of *Agrobacterium tumefaciens*," *Proc. Natl. Acad. Sci. USA*, 93: 126-130 (1996).

The *Arabidopsis* Genome Initiative, "Analysis of the genome sequence of the flowering plant *Arabidopsis thaliana*," *Nature*, 408: 796-815 (2000).

Virts et al., "Analysis of Transfer of Tumor-Inducing Plasmids from *Agrobacterium tumefaciens* to *Petunia* protoplasts," *Journal of Bacteriology*, 162 (3): 1030-1038 (1985).

Yin et al., "Evidence of multiple complex patterns of T-DNA integration into the rice genome," *Theor. Appl. Genet.*, 100: 461-470 (2000).

Yusibov et al., "Association of single-stranded transferred DNA from *Agrobacterium tumefaciens* with tobacco cells," *Proc. Natl. Acad. Sci. USA*, 91: 2994-2998 (1994).

Hoekema et al., "Delivery of T-DNA from the *Agrobacterium-Tumefaciens* Chromosome into Plant Cells," *EMBO*, 3(11): 2485-2490 (1984).

Lee, "Integration of genes into the chromosome of *Agrobacterium tumefaciens* C58," *Methods in Molecular Biology*, Humana Press Inc., pp. 55-66 (2006).

Lee et al., "Novel constructions to enable the integration of genes into the *Agrobacterium tumefaciens* C58 chromosome," *MPMI*, 14(4): 577-579 (2001).

Lee et al., "T-DNA binary vectors and systems," *Plant Physiology*, 146(2): 325-332 (2008).

Miranda et al., "*Agrobacterium-Tumefaciens* Transfers extremely Long T DNAs by a Unidirectional Mechanism," *Jrnl. Bacteriology*, 174(4): 2288-2297 (1992).

Sugita et al., "A transformation vector for the production of marker-free transgenic plants containing a single copy transgene at high frequency," *Plant Jrnl.*, 22(5): 461-469 (2000).

International Search Report issued in application No. PCT/US07/84668 (2008).

Kononov et al., "Integration of T-DNA binary vector 'backbone' sequences into the tobacco genome: evidence for multiple complex patterns of integration," *Plant J.*, 11:945-957 (1997).

Lee et al., "T-DNA Binary Vectors and Systems," *Plant Physiol.*, 146: 325-332 (2008).

* cited by examiner

SEQUENCE LISTING

```
<160> NUMBER OF SEQ ID NOS: 5

<210> SEQ ID NO 1
<211> LENGTH: 22
<212> TYPE: DNA
<213> ORGANISM: Artificial
<220> FEATURE:
<223> OTHER INFORMATION: Synthetic

<400> SEQUENCE: 1
gatctaccat gagcccagaa cg                                              22

<210> SEQ ID NO 2
<211> LENGTH: 22
<212> TYPE: DNA
<213> ORGANISM: Artificial
<220> FEATURE:
<223> OTHER INFORMATION: Synthetic

<400> SEQUENCE: 2
```

-continued cagatctcgg tgacgggcag ga                                              22

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
tcaccgtaac cagcaaatca                                                 20

<210> SEQ ID NO 4
<211> LENGTH: 20
<212> TYPE: DNA
<213> ORGANISM: Artificial
<220> FEATURE:
<223> OTHER INFORMATION: Synthetic

<400> SEQUENCE: 4
ctcggcacaa aatcaccact                                                 20

<210> SEQ ID NO 5
<211> LENGTH: 9189
<212> TYPE: DNA
<213> ORGANISM: Artificial
<220> FEATURE:
<223> OTHER INFORMATION: Synthetic

<400> SEQUENCE: 5
agtactttaa agtactttaa agtactttaa agtactttga tccaacccct ccgctgctat     60
agtgcagtcg gcttctgacg ttcagtgcag ccgtcttctg aaaacgacat gtcgcacaag    120
tcctaagtta cgcgacaggc tgccgccctg ccctttcct ggcgttttct tgtcgcgtgt     180
tttagtcgca taaagtagaa tacttgcgac tagaaccgga gacattacgc catgaacaag    240
agcgccgccg ctggcctgct gggctatgcc cgcgtcagca ccgacgacca ggacttgacc    300
aaccaacggg ccgaactgca cgcggccggc tgcaccaagc tgttttccga aagatcacc     360
ggcaccaggc gcgaccgccc ggagctggcc aggatgcttg accacctacg ccctggcgac    420
gttgtgacag tgaccaggct agaccgcctg gcccgcagca cccgcgacct actggacatt    480
gccgagcgca tccaggaggc cggcgcgggc ctgcgtagcc tggcagagcc gtgggccgac    540
accaccacgc cggccggccg catggtgttg accgtgttcg ccggcattgc cgagttcgag    600
cgttccctaa tcatcgaccg cacccggagc gggcgcgagg ccgccaaggc ccgaggcgtg    660
aagtttggcc ccgcccctac cctcacccccg gcacagatcg cgcacgcccg cgagctgatc    720
gaccaggaag gccgcaccgt gaaagaggcg gctgcactgc ttggcgtgca tcgctcgacc    780
ctgtaccgcg cacttgagcg cagcgaggaa gtgacgccca ccgaggccag gcggcgcggt    840
gccttccgtg aggacgcatt gaccgaggcc gacgccctgg cggccgccga gaatgaacgc    900
caagaggaac aagcatgaaa ccgcaccagg acgccagga cgaaccgttt tcattaccg     960
aagagatcga ggcggagatg atcgcggccg ggtacgtgtt cgagccgccc gcgcacgtct   1020
caaccgtgcg gctgcatgaa atcctggccg gtttgtctga tgccaagctg gcggcctggc   1080
cggccagctt ggccgctgaa gaaaccgagc gccgccgtct aaaaaggtga tgtgtatttg   1140
agtaaaacag cttgcgtcat gcggtcgctg cgtatatgat gcgatgagta aataaacaaa   1200
tacgcaaggg gaacgcatga aggttatcgc tgtacttaac cagaaaggcg ggtcaggcaa   1260
gacgaccatc gcaacccatc tagcccgcgc cctgcaactc gccggggccg atgttctgtt   1320

```
agtcgattcc gatccccagg gcagtgcccg cgattgggcg gccgtgcggg aagatcaacc   1380
gctaaccgtt gtcggcatcg accgcccgac gattgaccgc gacgtgaagg ccatcggccg   1440
gcgcgacttc gtagtgatcg acggagcgcc ccaggcggcg gacttggctg tgtccgcgat   1500
caaggcagcc gacttcgtgc tgattccggt gcagccaagc ccttacgaca tatgggccac   1560
cgccgacctg gtggagctgg ttaagcagcg cattgaggtc acggatggaa ggctacaagc   1620
ggcctttgtc gtgtcgcggg cgatcaaagg cacgcgcatc ggcggtgagg ttgccgaggc   1680
gctggccggg tacgactgc ccattcttga gtcccgtatc acgcagcgcg tgagctaccc   1740
aggcactgcc gccgccggca caaccgttct tgaatcagaa cccgagggcg acgctgcccg   1800
cgaggtccag gcgctggccg ctgaaattaa atcaaaactc atttgagtta atgaggtaaa   1860
gagaaaatga gcaaaagcac aaacacgcta agtgccggcc gtccgagcgc acgcagcagc   1920
aaggctgcaa cgttggccag cctggcagac acgccagcca tgaagcgggt caactttcag   1980
ttgccggcgg aggatcacac caagctgaag atgtacgcgg tacgccaagg caagaccatt   2040
accgagctgc tatctgaata catcgcgcag ctaccagagt aaatgagcaa atgaataaat   2100
gagtagatga attttagcgg ctaaaggagg cggcatggaa aatcaagaac aaccaggcac   2160
cgacgccgtg gaatgcccca tgtgtggagg aacgggcggt tggccaggcg taagcggctg   2220
ggttgtctgc cggccctgca atggcactgg aaccccaag cccgaggaat cggcgtgagc   2280
ggtcgcaaac catccggccc ggtacaaatc ggcgcggcgc tgggtgatga cctggtggag   2340
aagttgaagg ccgcgcaggc cgcccagcgg caacgcatcg aggcagaagc acgcccggt   2400
gaatcgtggc aagcggccgc tgatcgaatc cgcaaagaat cccggcaacc gccggcagcc   2460
ggtgcgccgt cgattaggaa gccgcccaag ggcgacgagc aaccagattt tttcgttccg   2520
atgctctatg acgtgggcac ccgcgatagt cgcagcatca tggacgtggc cgttttccgt   2580
ctgtcgaagc gtgaccgacg agctggcgag gtgatccgct acgagcttcc agacgggcac   2640
gtagaggttt ccgcagggcc ggccggcatg gccagtgtgt gggattacga cctggtactg   2700
atggcggttt cccatctaac cgaatccatg aaccgatacc gggaagggaa gggagacaag   2760
cccggccgcg tgttccgtcc acacgttgcg gacgtactca agttctgccg gcgagccgat   2820
ggcggaaagc agaaagacga cctggtagaa acctgcattc ggttaaacac cacgcacgtt   2880
gccatgcagc gtacgaagaa ggccaagaac ggccgcctgg tgacggtatc cgagggtgaa   2940
gccttgatta ccgcgctacaa gatcgtaaag agcgaaaccg gcggccgga gtacatcgag   3000
atcgagctag ctgattggat gtaccgcgag atcacagaag gcaagaaccc ggacgtgctg   3060
acggttcacc ccgattactt tttgatcgat cccggcatcg gccgttttct taccgcctg   3120
gcacgccgcg ccgcaggcaa ggcagaagcc agatggttgt tcaagacgat ctacgaacgc   3180
agtggcagcg ccggagagtt caagaagttc tgtttcaccg tgcgcaagct gatcgggtca   3240
aatgacctgc cggagtacga tttgaaggag gaggcggggc aggctggccc gatcctagtc   3300
atgcgctacc gcaacctgat cgagggcgaa gcatccgccg gttcctaatg tacgagcag   3360
atgctagggc aaattgccct agcaggggaa aaaggtcgaa aaggtctctt tcctgtggat   3420
agcacgtaca ttgggaaccc aaagccgtac attgggaacc ggaacccgta cattgggaac   3480
ccaaagccgt acattgggaa ccggtcacac atgtaagtga ctgatataaa agagaaaaaa   3540
ggcgattttt ccgcctaaaa ctctttaaaa cttattaaaa ctcttaaaac ccgcctggcc   3600
tgtgcataac tgtctggcca gcgcacagcc gaagagctgc aaaaagcgcc tacccttcgg   3660
tcgctgcgct ccctacgccc cgccgcttcg cgtcggccta tcgcggccgc tggccgctca   3720
```

```
aaaatggctg gcctacggcc aggcaatcta ccagggcgcg acaagccgc gccgtcgcca    3780
ctcgaccgcc ggcgcccaca tcaaggcacc ctgcctcgcg cgtttcggtg atgacggtga   3840
aaacctctga cacatgcagc tcccggagac ggtcacagct tgtctgtaag cggatgccgg   3900
gagcagacaa gcccgtcagg gcgcgtcagc gggtgttggc gggtgtcggg gcgcagccat   3960
gacccagtca cgtagcgata gcggagtgta tactggctta actatgcggc atcagagcag   4020
attgtactga gagtgcacca tatgcggtgt gaaataccgc acagatgcgt aaggagaaaa   4080
taccgcatca ggcgctcttc cgcttcctcg ctcactgact cgctgcgctc ggtcgttcgg   4140
ctgcggcgag cggtatcagc tcactcaaag gcggtaatac ggttatccac agaatcaggg   4200
gataacgcag gaaagaacat gtgagcaaaa ggccagcaaa aggccaggaa ccgtaaaaag   4260
gccgcgttgc tggcgttttt ccataggctc cgcccccctg acgagcatca caaaaatcga   4320
cgctcaagtc agaggtggcg aaacccgaca ggactataaa gataccaggc gtttccccct   4380
ggaagctccc tcgtgcgctc tcctgttccg accctgccgc ttaccggata cctgtccgcc   4440
tttctccctt cgggaagcgt ggcgctttct catagctcac gctgtaggta tctcagttcg   4500
gtgtaggtcg ttcgctccaa gctgggctgt gtgcacgaac cccccgttca gcccgaccgc   4560
tgcgccttat ccggtaacta tcgtcttgag tccaacccgg taagacacga cttatcgcca   4620
ctggcagcag ccactggtaa caggattagc agagcgaggt atgtaggcgg tgctacagag   4680
ttcttgaagt ggtggcctaa ctacggctac actagaagga cagtatttgg tatctgcgct   4740
ctgctgaagc cagttacctt cggaaaaaga gttggtagct cttgatccgg caaacaaacc   4800
accgctggta gcggtggttt ttttgtttgc aagcagcaga ttacgcgcag aaaaaaagga   4860
tctcaagaag atcctttgat cttttctacg ggtctgacg ctcagtggaa cgaaaactca    4920
cgttaaggga ttttggtcat gcatgatata tctcccaatt tgtgtagggc ttattatgca   4980
cgcttaaaaa taataaaagc agacttgacc tgatagtttg gctgtgagca attatgtgct   5040
tagtgcatct aacgcttgag ttaagccgcg ccgcgaagcg gcgtcggctt gaacgaattt   5100
ctagctagac attatttgcc gactaccttg gtgatctcgc cttttcacgta gtggacaaat   5160
tcttccaact gatctgcgcg cgaggccaag cgatcttctt cttgtccaag ataagcctgt   5220
ctagcttcaa gtatgacggg ctgatactgg gccggcaggc gctccattgc ccagtcggca   5280
gcgacatcct tcggcgcgat tttgccggtt actgcgctgt accaaatgcg ggacaacgta   5340
agcactacat ttcgctcatc gccagcccag tcgggcggcg agttccatag cgttaaggtt   5400
tcatttagcg cctcaaatag atcctgttca ggaaccggat caaagagttc ctccgccgct   5460
ggacctacca aggcaacgct atgttctctt gcttttgtca gcaagatagc cagatcaatg   5520
tcgatcgtgg ctggctcgaa gatacctgca agaatgtcat tgcgctgcca ttctccaaat   5580
tgcagttcgc gcttagctgg ataacgccac ggaatgatgt cgtcgtgcac aacaatggtg   5640
acttctacag cgcggagaat ctcgctctct ccaggggaag ccgaagtttc caaaaggtcg   5700
ttgatcaaag ctcgccgcgt tgtttcatca agccttacgg tcaccgtaac cagcaaatca   5760
atatcactgt gtggcttcag gccgccatcc actgcggagc cgtacaaatg tacggccagc   5820
aacgtcggtt cgagatggcg ctcgatgacg ccaactacct ctgatagttg agtcgatact   5880
tcggcgatca ccgcttcccc catgatgttt aactttgttt tagggcgact gccctgctgc   5940
gtaacatcgt tgctgctcca taacatcaaa catcgaccca ggcgtaacg cgcttgctgc    6000
ttggatgccc gaggcataga ctgtacccca aaaaaacagt cataacaagc catgaaaacc   6060
gccactgcgc cgttaccacc gctgcgttcg gtcaaggttc tggaccagtt gcgtgacggc   6120
```

```
agttacgcta cttgcattac agcttacgaa ccgaacgagg cttatgtcca ctgggttcgt    6180
gcccgaattg atcacaggca gcaacgctct gtcatcgtta caatcaacat gctaccctcc    6240
gcgagatcat ccgtgtttca aacccggcag cttagttgcc gttcttccga atagcatcgg    6300
taacatgagc aaagtctgcc gccttacaac ggctctcccg ctgacgccgt cccggactga    6360
tgggctgcct gtatcgagtg gtgattttgt gccgagctgc cggtcgggga gctgttggct    6420
ggctggtggc aggatatatt gtggtgtaaa caaattgacg cttagacaac ttaataacac    6480
attgcggacg tttttaatgt actgaattaa cgccgaattg ctctagcatt cgccattcag    6540
gctgcgcaac tgttgggaag ggcgatcggt gcgggcctct tcgctattac gccagctggc    6600 gaaagggggga tgtgctgcaa ggcgattaag ttgggtaacg ccagggtttt cccagtcacg    6660
acgttgtaaa acgacggcca gtccaagct aattcgcttc aagacgtgct caaatcacta    6720
tttccacacc cctatatttc tattgcactc ccttttaact gttttttatt acaaaaatgc    6780
cctggaaaat gcactccctt tttgtgtttg ttttttttgtg aaacgatgtt gtcaggtaat    6840
ttatttgtca gtctactatg gtggcccatt atattaatag caactgtcgg tccaatagac    6900
gacgtcgatt ttctgcattt gtttaaccac gtggatttta tgacatttta tattagttaa    6960
tttgtaaaac ctacccaatt aaagacctca tatgttctaa agactaatac ttaatgataa    7020
caattttctt ttagtgaaga aagggataat tagtaaatat ggaacaaggg cagaagattt    7080
attaaagccg cggtaagaga caacaagtag gtacgtggag tgtcttaggt gacttaccca    7140
cataacataa agtgacatta acaaacatag ctaatgctcc tatttgaata gtgcatatca    7200
gcatacctta ttacatatag ataggagcaa actctagcta gattgttgag cagatctcgg    7260
tgacgggcag gaccggacgg ggcggtaccg gcaggctgaa gtccagctgc cagaaaccca    7320
cgtcatgcca gttcccgtgc ttgaagccgg ccgcccgcag catgccgcgg ggggcatatc    7380
cgagcgcctc gtgcatgcgc acgctcgggt cgttgggcag cccgatgaca gcgaccacgc    7440
tcttgaagcc ctgtgcctcc agggacttca gcaggtgggt gtagagcgtg gagcccagtc    7500
ccgtccgctg gtgcggggg gagacgtaca cggtcgactc ggccgtccag tcgtaggcgt    7560
tgcgtgcctt ccaggggccc gcgtaggcga tgccggcgac ctcgccgtcc acctcggcga    7620
cgagccaggg atagcgctcc cgcagacgga cgaggtcgtc cgtccactcc tgcggttcct    7680
gcggctcggt acggaagttg accgtgcttg tctcgatgta gtggttgacg atggtgcaga    7740
ccgccggcat gtccgcctcg gtggcacggc ggatgtcggc cgggcgtcgt tctgggctca    7800
tggtagatcc cccgttcgta aatggtgaaa attttcagaa aattgctttt gctttaaaag    7860
aaatgattta aattgctgca atagaagtag aatgcttgat tgcttgagat tcgtttgttt    7920
tgtatatgtt gtgttgagaa ttaattctcg aggtcctctc caaatgaaat gaacttcctt    7980
atatagagga agggtcttgc gaaggatagt gggattgtgc gtcatccctt acgtcagtgg    8040
agatatcaca tcaatccact tgctttgaag acgtggttgg aacgtcttct ttttccacga    8100
tgctcctcgt gggtgggggt ccatctttgg gaccactgtc ggtagaggca tcttgaacga    8160 tagccttttcc tttatcgcaa tgatggcatt tgtaggagcc accttccttt tccactatct    8220
tcacaataaa gtgacagata gctgggcaat ggaatccgag gaggtttccg gatattaccc    8280
tttgttgaaa agtctcaatt gcccttttggt cttctgagac tgtatctttg atattttgg    8340 agtagacaag tgtgtcgtgc tccaccatgt tatcacatca atccacttgc tttgaagacg    8400
tggttggaac gtcttctttt tccacgatgc tcctcgtggg tgggggtcca tctttgggac    8460
cactgtcggc agaggcatct tcaacgatgg cctttccttt atcgcaatga tggcatttgt    8520
```

```
aggagccacc ttccttttcc actatcttca caataaagtg acagatagct gggcaatgga    8580
atccgaggag gtttccggat attacccttt gttgaaaagt ctcaattgcc ctttggtctt    8640
ctgagactgt atctttgata tttttggagt agacaagtgt gtcgtgctcc accatgttga    8700
cctgcaggca tgcaagcttg catgcctgca ggtcgactct agaggatccc cgggtaccga    8760
gctcgaattc gtaatcatgt catagctgtt tcctgtgtga aattgttatc cgctcacaat    8820
tccacacaac atacgagccg gaagcataaa gtgtaaagcc tggggtgcct aatgagtgag    8880
ctaactcaca ttaattgcgt tgcgctcact gcccgctttc cagtcgggaa acctgtcgtg    8940
ccagctgcat taatgaatcg gccaacgcgc ggggagaggc ggtttgcgta ttggagcttg    9000
agcttggatc agattgtcgt ttcccgcctt cagtttaaac tatcagtgtt tgacaggata    9060
tattggcggg taaacctaag agaaaagagc gtttattaga ataatcggat atttaaaagg    9120
gcgtgaaaag gtttatccgt tcgtccattt gtatgtgcat gccaaccaca gggttcccct    9180
cgggatcaa                                                             9189
```

BACKBONE-FREE LOW TRANSGENE COPY TRANSGENIC PLANTS

CROSS-REFERENCE TO RELATED PATENT APPLICATIONS

This application is a 35 U.S.C. §371 U.S. National Stage application of international patent application no. PCT/US2007/084668, filed Nov. 14, 2007, which claims priority to U.S. application No. 60/866,006, filed Nov. 15, 2006, the contents of which applications are incorporated herein by reference in their entireties.

The United States Government may have rights to this invention pursuant to NSF Fund No. 501-1392-0542, Award No. NTP0542.

BACKGROUND

*Agrobacterium tumefaciens* has been widely used for introduction of genes into plants for basic research as well as for generation of commercially used transgenic crops. For plant transformation, the gene of interest is placed between the left and right border repeats of *Agrobacterium* T-(transferred) DNA. Generally, the T-DNA region harboring the transgene is stably integrated into the plant genome by using an appropriate plant transformation protocol. T-DNA originates from the *Agrobacterium* Ti-(tumor inducing) plasmid, but because Ti-plasmids are large and difficult to manipulate, smaller T-DNA binary vectors are currently predominately used for generation of transgenic plants.

Despite the fact that *Agrobacterium* has been commonly used for plant transformation for more than two decades, some problems using this bacterium still remain: *Agrobacterium*-mediated transformation frequently results in unwanted high copy number T-DNA integration events. *Agrobacterium*-mediated transformation generally results in lower transgene copy numbers than do other transformation methods such as particle bombardment or polyethylene glycol-mediated transformation. However, multiple integration events, often coupled with inverted repeat T-DNA integration patterns, may affect the stability of transgene expression by silencing mechanisms. An additional problem with *Agrobacterium*-mediated transformation is the propensity for DNA sequences "outside" the T-DNA region to be carried along with or transferred independently of T-DNA and integrated into the plant genome. Integration of such vector "backbone" sequences can occur with high frequency. In one study, backbone sequences were detected in 75% of tested transgenic tobacco plants, and often the entire vector "backbone" is introduced into the plant genome. Although there is no evidence in the literature that the presence of vector backbone sequences affects transgene expression, T-DNA vector backbones usually harbor bacterial antibiotic resistance genes that can create governmental regulatory problems.

A current goal in agricultural biotechnology is to make plants with low (preferably single) transgene copy number, and no *Agrobacterium* T-DNA vector backbone sequence. A major goal of scientists generating transgenic plants is to have a single copy integrated transgene (less likely to have problems with silencing), and no T-DNA vector backbone integration (fewer regulatory problems). Therefore, methods and compositions to generate backbone-free, low transgene copy number plants are desired.

SUMMARY

Launching of T-DNA from the *Agrobacterium tumefaciens* chromosome reduces integrated transgene copy number and significantly reduces the presence of T-DNA backbone sequences. Providing a low-copy number vector that is capable of replicating in *Agrobacterium* may also result in transgenic plants with lower transgene copy number and lower vector backbone sequences.

A method of reducing transgene copy number and minimizing integration of vector backbone sequence in a transgenic plant includes:

(a) obtaining an *Agrobacterium* strain including a T-DNA sequence integrated into the *Agrobacterium* chromosome, wherein the T-DNA sequence includes a gene of interest flanked by T-DNA border repeat sequences; and (b) transforming a suitable host plant material with the *Agrobacterium*, thereby reducing transgene copy number and minimizing vector backbone sequence in the resulting transgenic plant.

A suitable *Agrobacterium* strain includes EHA101, GV3101, and LBA4404 and a suitable plant material includes plant material from monocots and dicots.

A method to generate a transgenic plant with a single transgenic copy of the gene of interest includes:

(a) obtaining an *Agrobacterium* strain including a T-DNA sequence integrated into the *Agrobacterium* chromosome, wherein the T-DNA sequence includes the gene of interest; and (b) transforming a suitable host plant material with the *Agrobacterium*, thereby generating the transgenic plant with a single copy of the gene of interest.

A method to generate a transgenic plant without any vector backbone sequence includes:

(a) obtaining an *Agrobacterium* strain including a T-DNA sequence integrated into the *Agrobacterium* chromosome, wherein the T-DNA sequence includes the gene of interest; and (b) transforming a suitable host plant material with the *Agrobacterium*, thereby generating the transgenic plant without any vector backbone sequence.

A method of obtaining an *Agrobacterium* strain capable of generating a transgenic plant with a single copy of a gene of interest in the absence of any vector backbone sequence includes:

(a) obtaining an integration vector including a gene of interest in a T-DNA sequence and a sequence to mediate chromosomal integration into the *Agrobacterium* chromosome; and (b) transforming the *Agrobacterium* with the integration vector; and (c) obtaining the *Agrobacterium* strain wherein the T-DNA is integrated into the *Agrobacterium* chromosome.

A method of reducing transgene copy number and minimizing integration of vector backbone sequence in a transgenic plant includes:

(a) obtaining a bacterial strain capable of transforming a plant cell, the bacterial strain comprising a DNA sequence of interest integrated into the bacterial chromosome, wherein the DNA sequence of interest is capable of being delivered into a plant cell; and (b) transforming a suitable host plant material with the bacterial strain, thereby reducing transgene copy number and minimizing vector backbone sequence in the resulting transgenic plant.

Suitable bacterial strains capable of transforming plant cells are selected from the group of *Agrobacterium* spp., *Bradyrhizobium* spp., *Rhizobium* spp., *Mesorhizobium* spp., *Ochrobactrum* spp., *Sinorhizobium* spp., and *Phyllobacterium* spp. These bacterial species are capable of transferring DNA into a plant cell.

An *Agrobacterium* strain suitable for the methods described herein includes a T-DNA integrated into a chromosome of the *Agrobacterium*.

An *Agrobacterium* chromosomal integration vector includes a T-DNA and capable of integrating the T-DNA into the chromosome of the *Agrobacterium*, and for example a T-DNA is inserted into the pica locus of the *Agrobacterium* chromosome. Any locus in *Agrobacterium* chromosome is suitable for use as a launching pad for T-DNA as long as the locus does not affect the growth and transformation ability of the *Agrobacterium*.

DETAILED DESCRIPTION

Figure 1A:
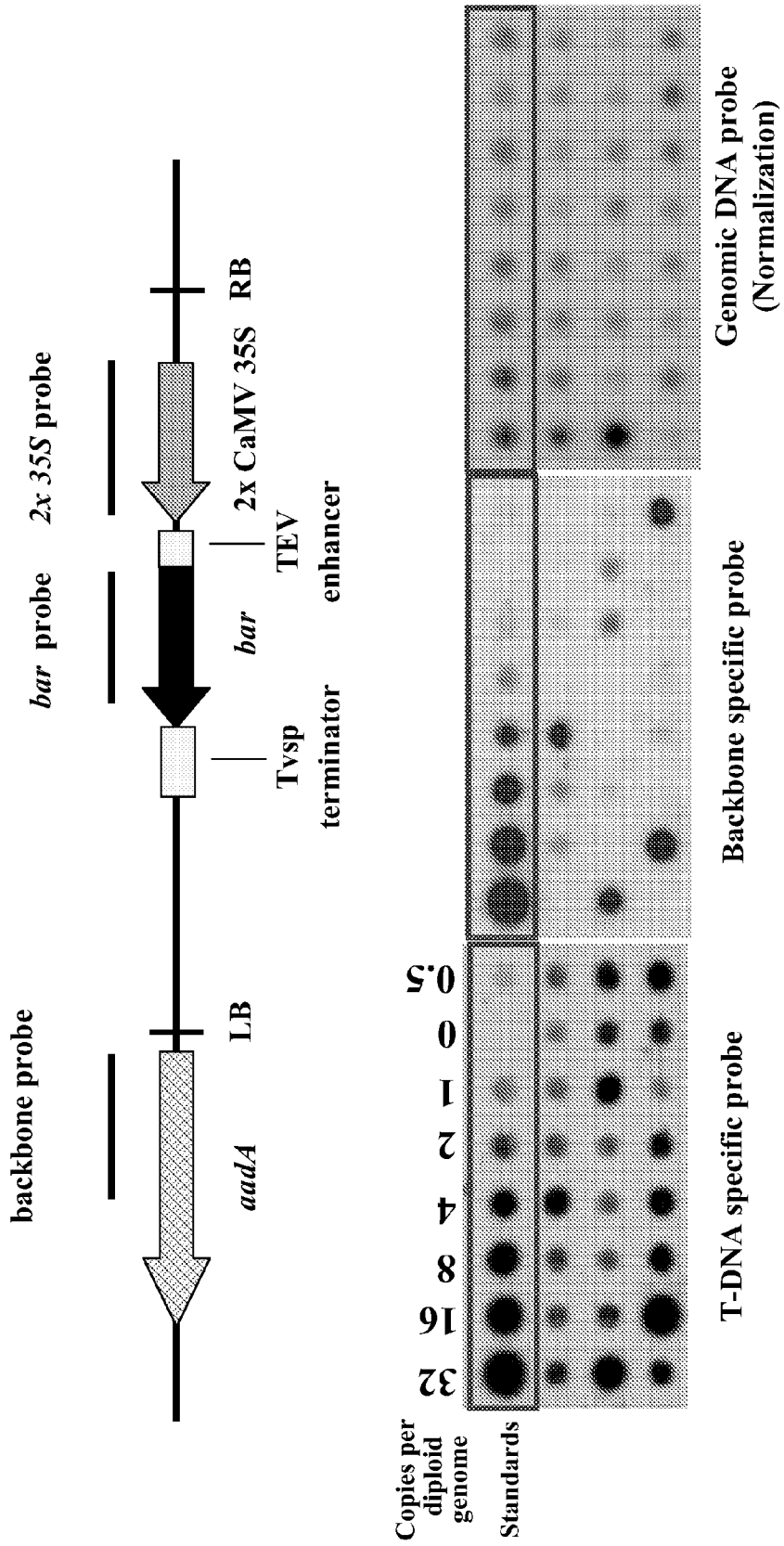
FIG. 1A shows a schematic map of the T-DNA and neighboring regions used in constructing the various vectors described herein and the results of DNA dot blot analysis for transgene copy number and backbone integration. In the vector map, black lines (probes) represent fragments used for hybridization experiments. LB and RB: T-DNA left and right borders, respectively; aadA, gene encoding spectinomycin resistance; TEV: enhancer, translational leader from Tobacco Etch Virus.

Integration of T-DNA into the *Agrobacterium tumefaciens* chromosome reduces integrated transgene copy number and significantly reduces the presence of T-DNA backbone sequences. Providing a low-copy number vector that is capable of replicating in *Agrobacterium* also results in transgenic plants with lower transgene copy number and lower vector backbone sequences.

Fourteen combinations of T-DNA binary vector systems with various commonly used *Agrobacterium* strains were tested in *Arabidopsis* and maize. Transformation frequency, average integrated transgene copy number, % of transgenic plants with a single inserted transgene, and % of plant with no integrated vector backbone sequences were determined following transformation experiments. *Agrobacterium* strains containing T-DNA integrated into, and "launched" from, the *Agrobacterium* chromosome generated lower transgene copy number that were vector backbone-free, as opposed to commonly used T-DNA plasmid binary vectors.

The effect of three commonly used *A. tumefaciens* strains and five T-DNA replication origins on transformation efficiency and the "quality" of T-DNA integration events in *Arabidopsis thaliana* and maize were analyzed. Integration of T-DNA into the *Agrobacterium* chromosome rather than by use of T-DNA binary vectors, surprisingly, resulted in fewer integrated transgenes and almost eliminated the presence of T-DNA binary backbone sequences in plants. These two aspects of plant transformation were accompanied by a decreased transformation frequency. In *Arabidopsis*, this decrease is slight (2- to 4-fold), but somewhat more substantial in maize (5- to 10-fold). However, this decrease in transformation frequency or efficiency is generally offset by the increased likelihood of generating single copy transgenic plant that is vector backbone-free.

Stable and predictable transgene expression has become a major objective for both basic and applied research. Multiple integrated T-DNA copies, especially when combined with complex T-DNA integration patterns, can trigger transgene silencing. The routine generation of single-copy transgenic events is therefore a major goal for agricultural biotechnology. "Launching" T-DNA from the *Agrobacterium* chromosome, as disclosed herein, thus, provides a novel approach to improve plant biotechnology.

Several studies have analyzed T-DNA locus and/or copy numbers in transgenic *Arabidopsis*. A report concluded that the average number of independently segregating, active transgene loci in an initial library of T-DNA tagged plants is 1.4. This value is similar to that of other T-DNA tagged collections in *Arabidopsis*. However, the number of active loci in these plants is generally less than the number of integrated T-DNA molecules. T-DNA insertions are frequently arranged as concatemers in directly or inverted repeat orientation. A report showed that 70% of tested *Arabidopsis* transformants generated by a vacuum infiltration protocol carried direct or indirect tandem repeat copies of T-DNA. In the present disclosure, the average T-DNA copy number in *Arabidopsis* ranged between 1.0 and 5.1, and in maize between 1.3 and 3.9 transgene copies per diploid genome (FIG. 4).

Interestingly, the average transgene copy number of both maize and *Arabidopsis* plants that were generated by transformation using *A. tumefaciens* LBA4404 was lower than that resulting from transformation using the other tested strains. The *Agrobacterium* strain, transformation method, and plant target tissue may influence the number of integrated T-DNA molecules.

Although T-DNA integration into the plant genome was experimentally shown almost 30 years ago, details are not known about how many T-DNA strands are produced in *Agrobacterium* and transferred to the plant cell. It is likely that considerably more T-strands are transferred than are integrated. T-DNA copy number in *Agrobacterium* differs with the various replication origins that were used. The T-DNA copy number of the T-DNA chromosomal integration construction in the bacterial cell is '1' (except during replication before cell partition). Low integrated transgene copy numbers in plants may result from a limited number of T-strands transferred to the plant cell. A report showed that T-DNA molecules delivered by mixed infection of various *Agrobacterium* strains could co-integrate. The integration of more than one T-DNA likely results from co-delivery of T-DNAs from two different *Agrobacterium* cells. However, if a low T-DNA copy number in *Agrobacterium* results in a low integrated transgene copy number in transformed plant cells, it would have been expected to see a correlation between bacterial and plant T-DNA copy number using the different T-DNA replication origins because they replicate to different extents in the bacteria. Surprisingly, however, contrary to expectations, such a correlation was not present, based on the results disclosed herein for the binary vectors tested.

Figure 4A:
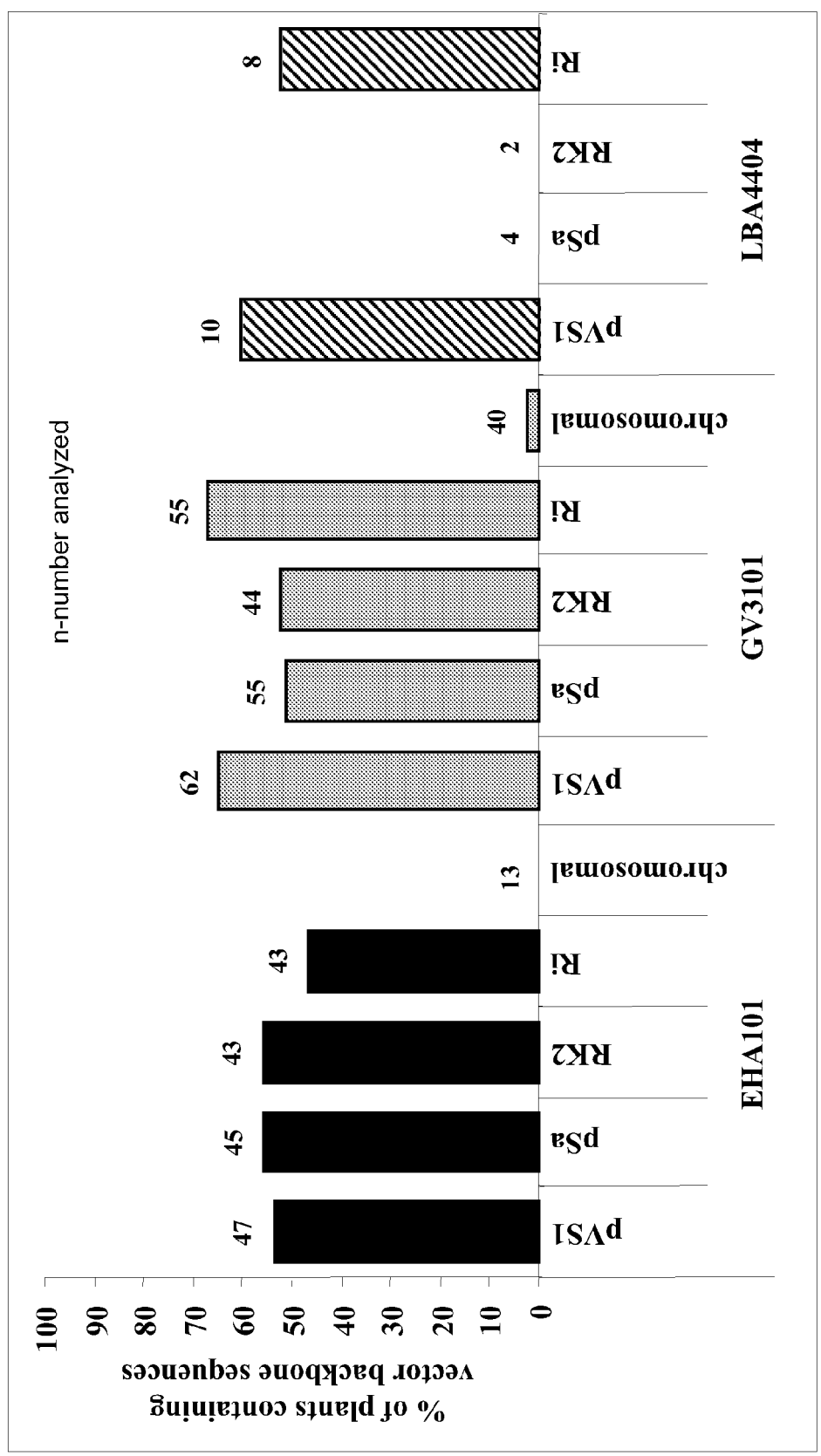
FIG. 4 shows the percentage of plants containing vector backbone sequences following transformation by the 14 T-DNA replication origin-by-*Agrobacterium* strain combinations for *Arabidopsis thaliana* (A) and maize (B). Blots were hybridized with a backbone-specific probe, the aadA gene (FIG. 1). Numbers over the bars represent the number of independent events analyzed.
Figure 4B:
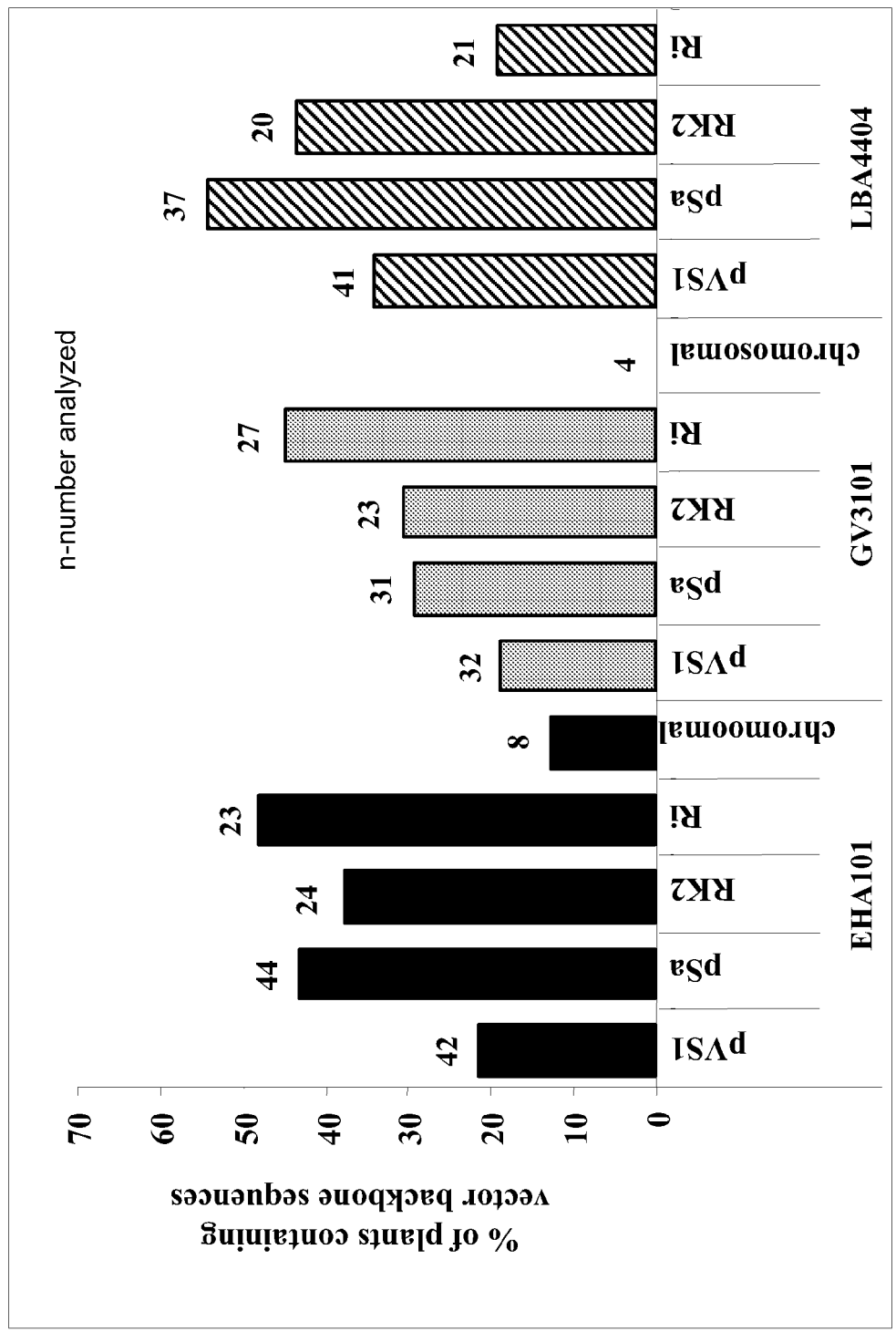

Based on the data presented herein, the integration of T-DNA into the *Agrobacterium* chromosome almost eliminated the presence of T-DNA backbone sequences in both transgenic maize and *Arabidopsis* plants. Integration of binary vector backbone sequences is a common phenomenon observed in many plant transformations. Almost no backbone DNA was present in plants when plants were transformed with an *Agrobacterium* strain that carried the T-DNA on the chromosome (FIG. 4A). Similar results were obtained in maize transformation experiments (FIG. 4B). In contrast, 47-67% of the *Arabidopsis* plants generated by *Agrobacterium* strains harbouring a T-DNA binary vector contained integrated vector backbone sequences. An earlier report detected vector backbone sequences in 62% of the transgenic *Arabidopsis* plants produced by a vacuum infiltration transformation protocol, and another report detected vector backbone sequences in 68-79% of the transgenic *Arabidopsis* plants produced using a floral dip transformation protocol.

Vector backbone sequences relate to any portion of the vector sequence that is present outside of either the left border (LB) or the right border (RB) of the T-DNA sequence. The vector backbone sequence that is integrated may be positioned adjacent and contiguous to the LB or the RB or the backbone sequence may be positioned at a certain distance from the LB or the RB, i.e., the vector backbone sequence may be positioned non-adjacent to the T-DNA. The presence of the vector backbone sequence can be verified by dot blot hybridization with appropriate vector-derived probes, or by PCR amplification using appropriate primers, or by sequencing plant genomic DNA with appropriate sequence-specific primers. Methods and compositions described herein generate transgenic plants without any vector backbone sequence or transgenic plants that have vector backbone sequences less than about 1% or less than about 5% or less than about 10% of the transformed plants. The length of the vector backbone may range from 1 or 2 base pairs, or about 100-500 base pairs or to about a few kilo bases.

Transformation of plants with an *Agrobacterium* strain with a T-DNA integrated in the chromosome results in transgenic plants with vector backbone sequence in less than 10% of the transformed plants, or less than about 5% of the transformed plants or less than about 1% of the transformed plants. In preferred embodiments, all of the transformed plants contain transgenic DNA without any vector backbone sequence.

The percentage of T-DNA single copy plants obtained using the methodologies disclosed herein range from about 50-60 or about 50-75 or about 75-85 or about 85-90 or about 90.

Transfer of binary vector backbone sequences can occur when the T-DNA left border repeat is not recognized by the VirD2 endonuclease during processing of the T-DNA strand. It can also occur as a result of VirD2 linkage to the 5' end of the vector DNA directly outside the T-DNA left border, followed by transfer of the backbone in a manner analogous to that of T-DNA transfer. If the T-DNA strand is derived from a binary plasmid and during T-DNA processing the left border repeat is skipped, T-DNA processing will either end at a sequence in the backbone that resembles a T-DNA border or, due to the circular nature of binary vectors, when the right border repeat is reached. However, if T-DNA is integrated into the bacterial chromosome, read-through at the T-DNA left border repeat could result in very long T-DNAs, theoretically as long as the *Agrobacterium* chromosome itself if no adequate termination site is present. It is not fully known why transfer of long T-DNA, although possible, is less frequent than transfer of small T-DNAs. When the right border of a Ti-plasmid was inverted, at low frequency, the entire 190 kbp Ti-plasmid became integrated into the plant genome.

If the T-DNA left border is skipped during T-DNA strand processing (or if DNA transfer initiates from sequences directly to the left of the left T-DNA border), the resulting T-DNA may be too long for efficient transfer to the plant or integration into the plant genome. Although there might be concern that sequences from the bacterial chromosome next to the T-DNA right border could be integrated into the plant genome, probing of the DNA membranes with an *Agrobacterium* aadA fragment failed to detect its presence.

It is possible that the integration of vector backbone sequences into plants is a consequence of simplifying *Agrobacterium*-mediated plant transformation by the use of small T-DNA binary vectors. Transfer of non-T-DNA portions of a large Ti-plasmid to plants is possible but rare: On average only 1 out of 80 transgenic tobacco calli contained a nptII gene positioned outside the T-DNA left border. Vector backbone sequences were detected in ~75% of transgenic tobacco plants generated using an *Agrobacterium* strain carrying a small T-DNA binary vector. These results indicate that backbone integration occurs more frequently when a small T-DNA binary vector is used. T-DNA binary vectors are ubiquitously used because of their ease of handling. Vector systems have been built to simplify integration of T-DNA into the *Agrobacterium* chromosome (see for example, Lee et al., 2001, the disclosure of which is herein incorporated by reference).

When generating transgenic plants, it is generally preferred to use *Agrobacterium* strains that confer high transformation frequencies because this could reduce both personnel and materials costs. Based on the data presented herein *A. tumefaciens* LBA4404 showed low transformation frequencies for *Arabidopsis thaliana* but transformed maize efficiently (compare FIGS. 2A and 2B). In addition, GV3101 showed the lower transformation frequencies for maize, and in contrast it was more efficient for *Arabidopsis* transformation. Interestingly, except for the chromosomal integration constructions, a strict correlation between transformation frequency and integrated transgene copy numbers was not observed. This observation contradicts a generally prevalent concept that *Agrobacterium* strains which mediate high transformation frequencies are likely to cause high integrated transgene copy numbers.

Any suitable locus or target on an *Agrobacterium* chromosome can be used as long as (i) insertion at a locus does not significantly alter bacterial growth and viability, and (ii) insertion at a locus does not significantly impede the transformation process (e.g., insertion into a chromosomal virulence gene).

*Agrobacterium* spp., *Rhizobium* spp., *Sinorhizobium* spp., *Mesorhizobium* spp., *Phyllobacterium* spp. *Ochrobactrum* spp. and *Bradyrhizobium* spp. are suitable for use in plant transformation employing the methods and compositions described herein. Chromosomal integration vectors are identified based on the known sequences of one or more loci of the bacterial species capable of transforming plants. Many of the non-Agrobacterium spp. may be equipped with one or more genes or plasmids derived from *Agrobacterium* to render them capable of transforming plants. Some examples of *Agrobacterium tumefaciens* strains include for example, EHA101, GV3101, LBA4404, EHA105, AGL0, and AGL1, LBA4404. Other *Agrobacterium* species include for example, *Agrobacterium vitis* (K252), or *Agrobacterium rhizogenes* (A4).

One or more components of a chromosomal integration vector or any vector used herein may be operatively coupled to one or more promoter sequences. For example, a gene of interest may be linked to a tissue specific promoter and a selectable marker may be operatively coupled to a constitutive promoter. Appropriate translation termination signals can be incorporated into the vector.

A "universal recipient strain" (e.g., a universal *Agrobacterium* recipient strain) is developed, where the T-DNA is already integrated in a suitable chromosomal locus (e.g., in the pica locus of the *Agrobacterium* chromosome). This T-DNA may have a suitable selectable marker (e.g., bar gene) and a small portion/fragment/region of a suitable vector sequence (e.g., pbluescript or any other commonly used bacterial cloning vector). This recipient strain is used in conjunction with any suitable vector (e.g., pbluescript/puc-derived cloning vector (such as the pSAT vectors) that has a promoter, gene, and polyA. When this cloning vector is introduced into *Agrobacterium*, it cannot replicate. However, it can recombine with the small portion of the cloning vector sequence (e.g., pbluescript) that is already inserted into the T-DNA. For example, a promoter-gene-polyA construct is made and is transformed into *Agrobacterium* and selected for any suitable marker encoded on the cloning vector (e.g., carb-resistance encoded on the pSAT vector). If the *Agrobacterium* strain is resistant to the marker encoded on the cloning vector, then the cloning vector sequence has co-integrated (recombined) into the T-DNA on the chromosome. Such co-integration can be experimentally verified by DNA blot hybridization.

Unlike accidental or passive integration of T-DNA into *Agrobacterium* chromosomes, present methods and compositions provide active and direct methods to use *Agrobacterium* chromosomes as specific launching pads for transferring T-DNA into a plant cell and thereby directly minimizing transgene copy number and reducing vector backbone integration in the transgenic plants. Thus, the chromosomal vectors described herein target specific loci in *Agrobacterium* chromosomes. The T-DNA used herein generally contains one or more genetic elements that are heterologous to *Agrobacterium* or any other bacterial species used in plant transformations.

A transgenic crop plant contains an exogenous polynucleotide molecule or a heterologous transgene either inserted into the genome of a crop plant cell or transiently expressed without stable integration. Suspension cultures, embryos, meristems, callus tissue, leaves, roots, shoots, gametophytes, sporophytes, ovules, pollen and microspores, and seeds, and fruit are generally referred to as plant material.

The vectors described herein may also include a coding region for a plant selectable marker gene, which may be located in the T-DNA, to select transformed plant cells with the corresponding reagent. The plant selectable marker may provide resistance to a positive selection compound, for example, antibiotic resistance (e.g., kanamycin, hygromycin), or herbicide resistance.

The vectors described herein may also include one or more reporter genes. A reporter gene may be present in addition to a selectable marker. Examples of reporter genes include for example, the beta-glucuronidase (GUS), the chloramphenicol acetyl transferase, the green fluorescent protein (GFP) and luciferase.

Methods for transforming a plant cell include for example contacting at least a plant cell with a transformation bacteria of the present invention; and selecting the plant cell transformed with one or more heterologous transgenes.

Agronomically important traits such as improved nutritional value, increased biomass, resistance to environmental hazards such as drought, salinity, pathogens are engineered into a plant species of interest using the methods described herein. Any agriculturally relevant trait capable of being manipulated genetically is suitable to implement using the methods disclosed herein.

Any plant species that can be genetically transformed using a bacterial transformation system (e.g., *Agrobacterium*) is suitable. Suitable plant species include for example, apple, barley, canola, coffee, corn, cotton, grape, lettuce, lemon, lime, maize, mushroom, oat, peanut, pear, pepper, potato, rice, rye, sorghum, soybean, sugarbeet, sugarcane, sunflower, tobacco, tomato, and wheat. Suitable plants include both monocots and dicots.

EXAMPLES

The following examples are for illustrative purposes and are not intended to limit the scope of the disclosure.

Example 1

A. tumefaciens strains and T-DNA Constructions

It was investigated whether different *Agrobacterium* strains and binary vector systems affect transformation frequency, integrated transgene copy number, and the frequency of T-DNA backbone integration events. Investigation utilized various combinations of the commonly used *A. tumefaciens* strains EHA101, GV3101, and LBA4404 with five different T-DNA binary systems. These *Agrobacterium* strains are non-oncogenic ("disarmed") and have been used for transformation of a large variety of plants. EHA101 (Hood et al., (1987), *Plant Physiol.* 83:529-534) harbours a derivative of the agropine/L, L-succinamopine-type Ti-plasmid pTiBo542, GV3101 (Koncz and Schell, (1986), *Mol. Gen. Genet.* 204:383-396), a derivative of the nopaline-type Ti-plasmid pTiC58, and LBA4404 (Ooms et al., (1981), *Gene* 14:33-50) a derivative of the octopine-type Ti-plasmid pTi-Ach5. The tested T-DNA vectors contain identical T-DNA regions plus an aadA gene for bacterial selection for spectinomycin resistance. However, they contain different origins of replication (ori) resulting in different T-DNA copy numbers in the bacterial cell: the pVS ori (about 5 copies/cell), the pSa ori (about 3 copies/cell), the RK2 ori (about 5-10 copies/cell), and the pRiA4b ori (15-20 copies/cell for the ori fragment used in these constructions). The effect of integration of T-DNA into the *Agrobacterium* C58 chromosome at the picA locus in strains EHA101 and GV3101 were analyzed. T-DNA integration into this locus does not affect transformation and vectors specifically designed to integrate genes into this locus by homologous recombination are described in Lee et al., (2001), incorporated herein by reference (Lee et al., (2001) Mol. Plant-Microbe Interact. 14:577-579).

A total of 14 different *A. tumefaciens* strains (by replication origin combinations) were analyzed. The T-DNA region, derived from the binary vector pTF101.1, harbours a bar gene as a plant selectable marker (de Block et al., (1987), *EMBO J.* 6:2513-2518) under the control of a CaMV double 35S promoter (FIG. 1) (SEQ ID NO: 5). Utilizing identical T-DNA regions with the same plant selectable marker and the identical non-T-DNA sequence proximal to the T-DNA left border in all constructions enabled to compare results obtained for transformation frequencies, integrated transgene copy numbers, and backbone integration for all strain-by-construct combinations.

Example 2

Effect of *A. tumefaciens* Strain and T-DNA Ori on Transformation Frequency

Figure 2A:
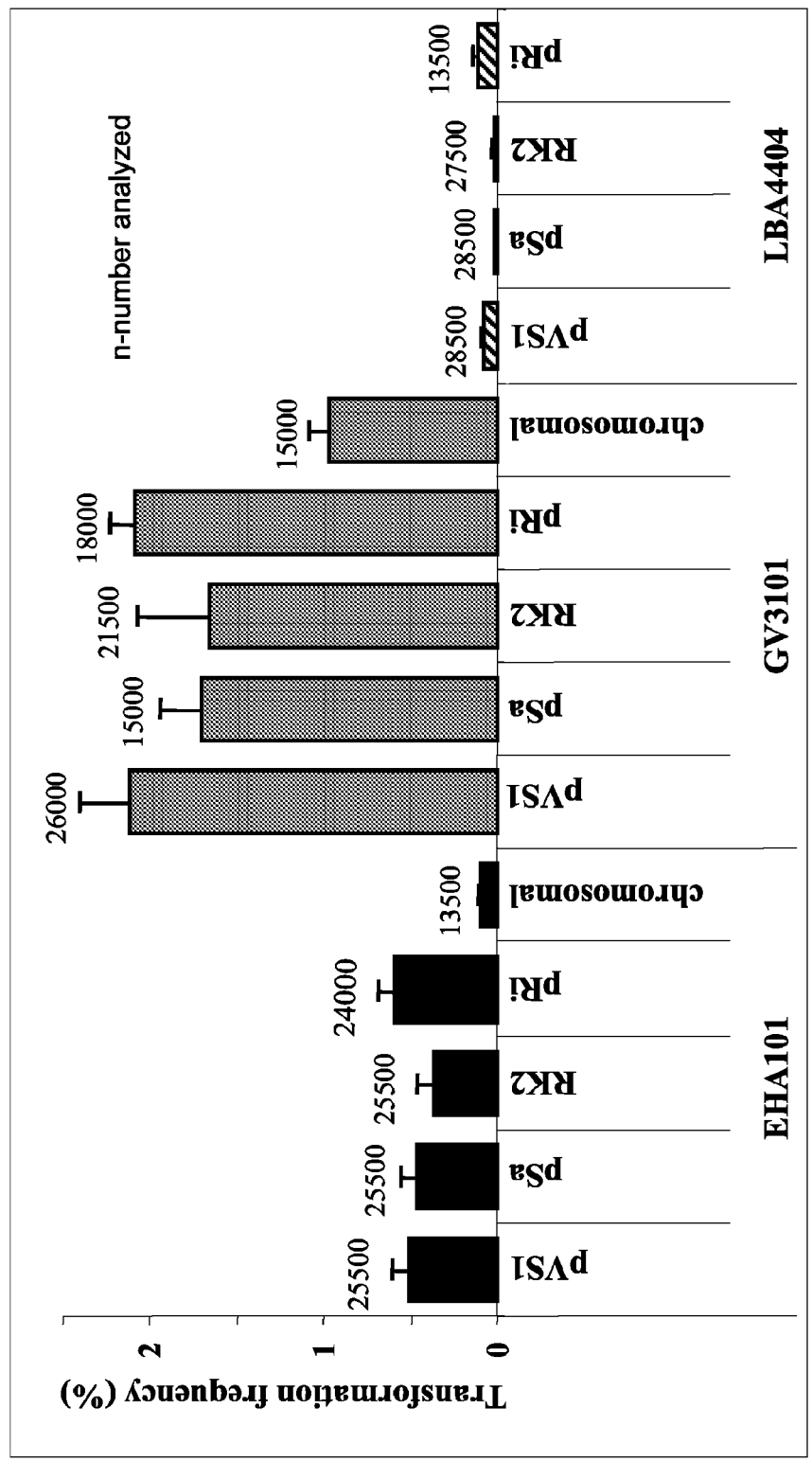
FIG. 2 shows transformation frequencies of *Arabidopsis thaliana* (A) and maize (B) with different *Agrobacterium* strain-by-origin of replication origin combinations. *Arabidopsis thaliana* was transformed by a floral dip protocol, and maize was transformed by embryo inoculation protocol. Error bars represent the standard error among different transformation experiments. At least 5 independent transformation experiments were conducted for both *Arabidopsis thaliana* and maize. The total number of analyzed seeds for *Arabidopsis* (A) or infected embryos for maize (B) are indicated above each error bar.

The effect of 14 *Agrobacterium* strain-by-construct combinations on transformation frequency in *Arabidopsis thaliana* and *Zea maize* were determined. *Arabidopsis thaliana* was transformed using a floral dip protocol (Clough and Bent, (1998), *Plant J.* 16:735-743). At least five transformation experiments were conducted for each vector-by-strain combination, and transformation frequencies were determined by analyzing 1500-4500 seeds for each experiment. FIG. 2A shows the transformation frequencies for *Arabidopsis* grouped as strain-by-replication origin combinations. Transformation frequency was dependent upon the *A. tumefaciens* strain utilized. In the data presented herein, GV3101 resulted in the highest transformation frequencies (0.97-2.11%), whereas EHA101 and LBA4404 effected medium (0.09-0.58%) and low (0.01-0.12%) transformation frequencies. T-DNA replication origin, as part of the binary vector, had little effect on transformation frequency with one significant exemption: Integration of T-DNA into the *Agrobacterium* chromosome of both EHA101 and GV3101 resulted in transformation frequencies lower than those of the other four T-DNA binary systems of the respective strain. For EHA101 the transformation frequency is 4- to 5-fold lower, whereas for GV3101 the frequency is 2-fold lower compared to the binary systems tested (FIG. 2A). Integration of the T-DNA region into the pica locus of the Ach5 chromosome of *A. tumefaciens* LBA4404 was not achieved, probably because the picA sequence of this chromosome does not share enough similarity with the pica sequence of the vector that was designed which derives from the C58 chromosome (Lee et al., 2001).

Figure 2B:
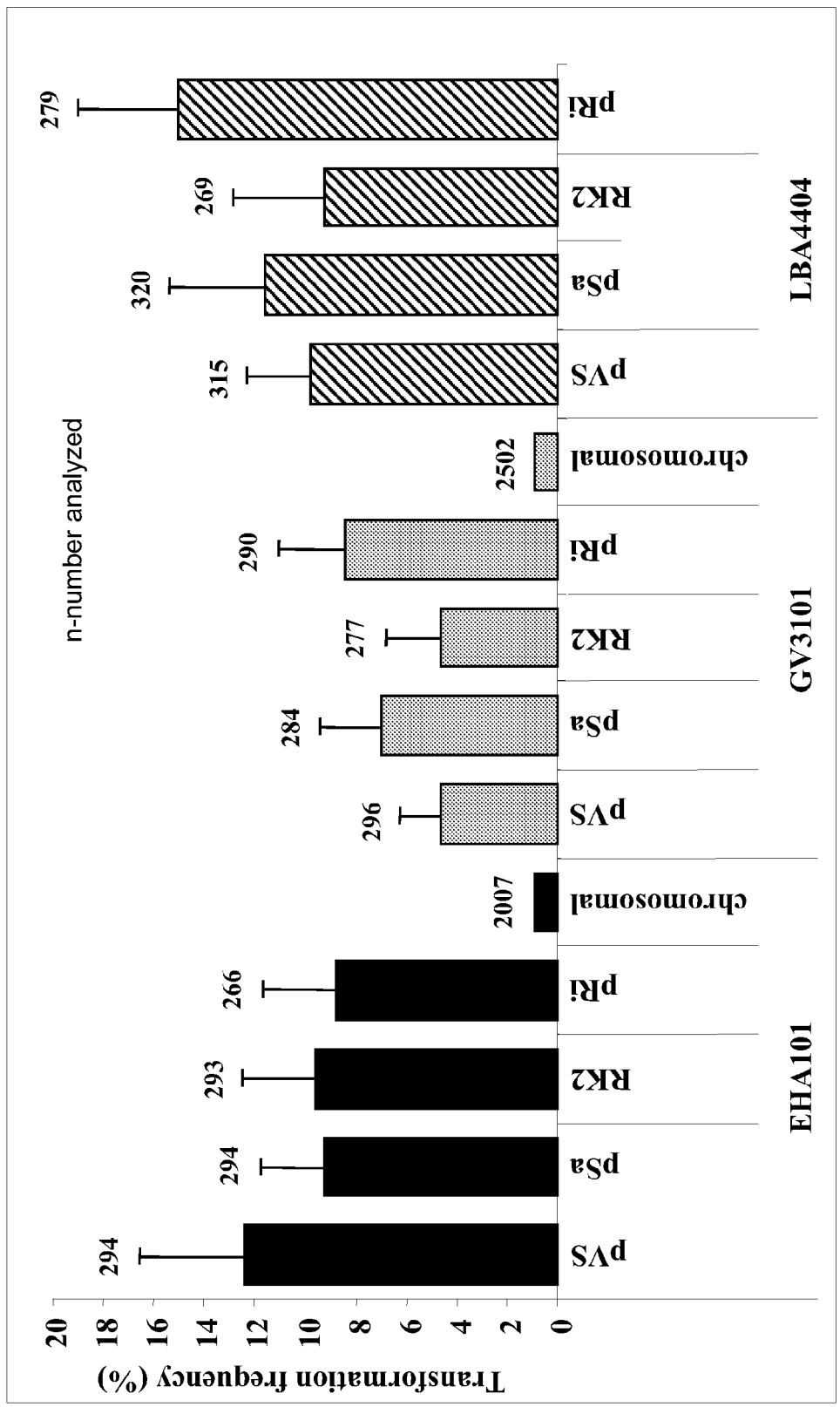

Maize was transformed by an embryo inoculation protocol, and 5-7 independent transformation experiments were conducted for each strain-by-replication origin combination. Transformation frequencies of the 14 combinations are shown in FIG. 2B, and range between 0.9% and 15%. As seen for *Arabidopsis*, integration of T-DNA into the chromosomes of EHA101 and GV3101 resulted in low transformation frequencies (0.9%), whereas transformation frequencies were considerably higher (5-15%) when T-DNA was placed on a binary vector.

In general, in the data presented herein for maize transformation, *A. tumefaciens* EHA101 and LBA4404 effected the highest transformation frequencies (range among the replication origins: 9-15% and 9-12%, respectively), whereas the transformation frequency using GV3101 was lower (5-8%) (FIG. 2B). Except for the two strains in which T-DNA was integrated into the chromosome, the T-DNA binary vector replication origin did not significantly affect transformation frequency under the conditions tested. However, the integration of the T-DNA into a chromosomal locus significantly affected the transformation frequency.

Example 3

Bacterial Chromosomal Integration of T-DNA Results in a Higher Percentage of Plants Containing a Single T-DNA Copy The number of copies of integrated T-DNA in transgenic plants was investigated by DNA dot blot hybridization. Addition of various amounts of pTF101.1 DNA to wild-type plant genomic DNA served as copy number reconstruction controls. Calculations for T-DNA copy number standards were based on an *Arabidopsis* genome size of 125 Mbp (The *Arabidopsis* genome initiative, 2000) and a maize genome size of 2500 Mbp. The size of pTF101.1 is 9189 bp.

Figure 3A:
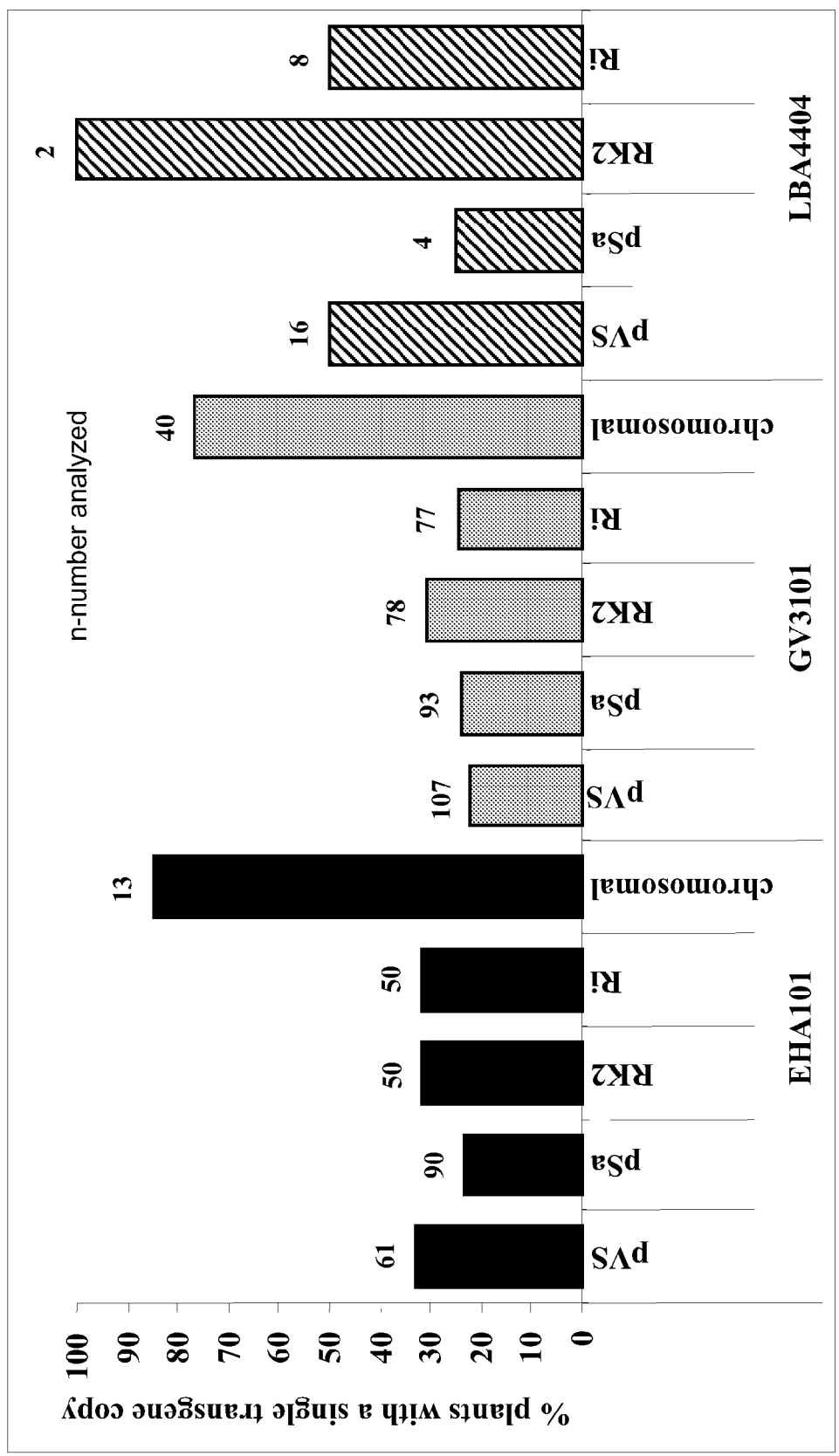
FIG. 3 shows the percentage of plants containing a single copy of integrated T-DNA following transformation by the 14 T-DNA replication origin-by-Agrobacterium strain combinations for *Arabidopsis thaliana* (A) and maize (B). Copy number reconstructions were done by DNA dot blot experiments using T-DNA specific probes (FIG. 1). Analysis was performed on heterozygous T1 generation *Arabidopsis thaliana* plants and heterozygous regenerated T0 generation maize plants. Numbers over the bars represent the number of independent events analyzed.

T1 generation (heterozygous for T-DNA) *Arabidopsis* plants were analysed using a bar gene-specific fragment (FIG. 1). FIG. 3A shows the percentage of plants containing a single transgene copy grouped as various strain-by-replication origin combinations. The percentage of single copy plants spans a wide range between 22% (GV3101, pVS1 origin of replication) and 100% (LB4404, RK2 origin of replication). However, because of the extremely low transformation frequency, only two plants were obtained for the LB4404-by-RK2 origin combination. Interestingly, placement of T-DNA into the *Agrobacterium* chromosomal picA locus, rather than on a T-DNA binary vector, resulted in 85% of the plants infected with EHA101 and 75% of the plants infected with GV3101 containing a single transgene copy. The percentage of T-DNA single copy plants resulting from other EHA101 and GV3101 replication origin combinations (T-DNA on a binary vector)

was much lower. Only 23-33% (EHA101) or 22-34% (GV3101) of the plants contained single copy transgenes.

Because of the low transformation efficiency of *Arabidopsis thaliana* with LBA4404 (FIG. 2A), only a few plants were obtained for analysis. The percentage of single transgene integration events of three of the four analyzed T-DNA binary vector replication origins in LBA4404 is higher than that of the respective replication origins in the other two bacterial strains (50-100% for LBA4404 versus 22-34% for EHA101 and GV3101).

Figure 5A:
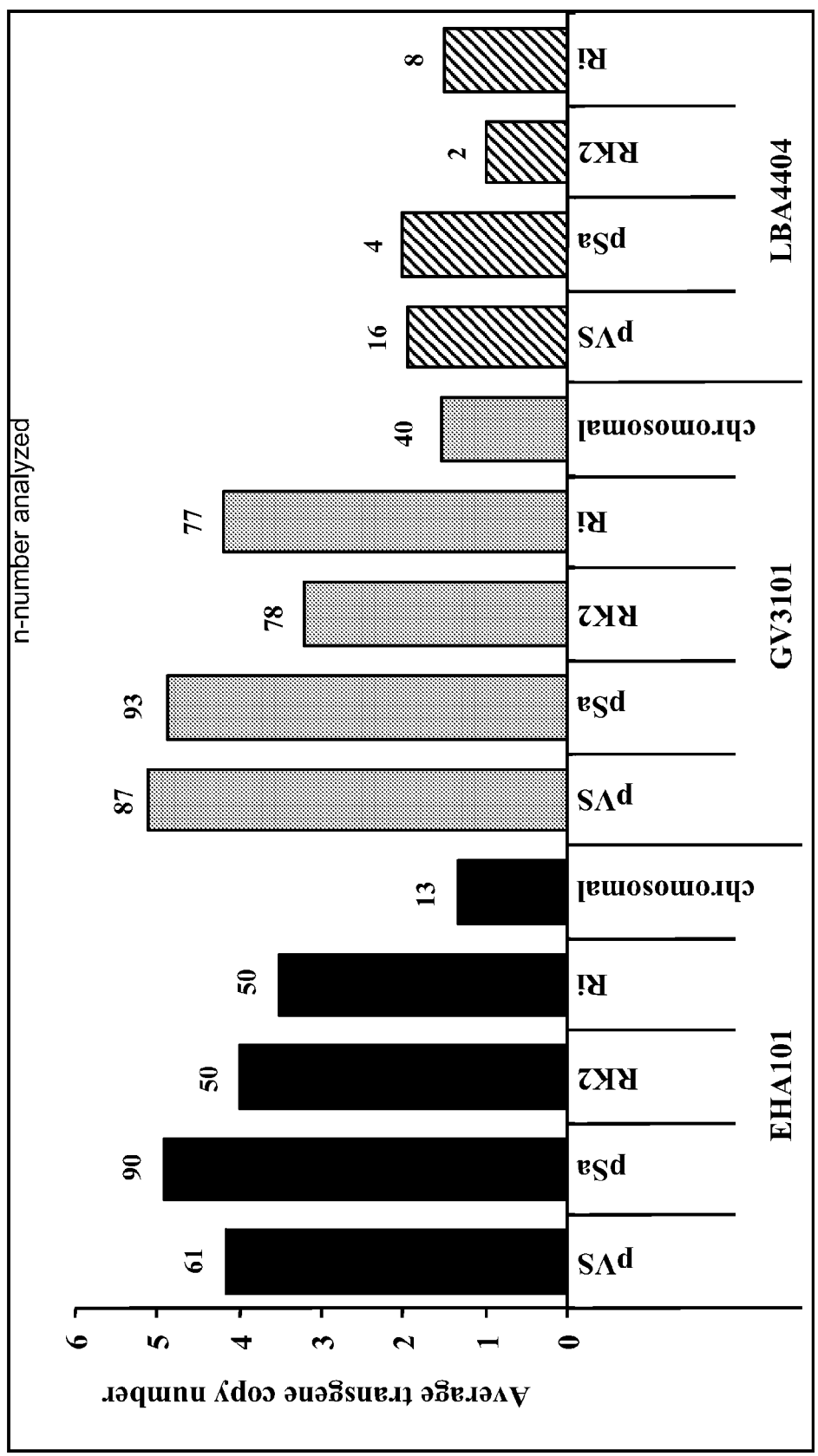
FIG. 5 shows average transgene copy number for 14 T-DNA replication origins-by-*A. tumefaciens* strain combinations for *Arabidopsis thaliana* (A) and maize (B). Numbers over the bars represent the number of independent events analyzed.
Figure 5B:
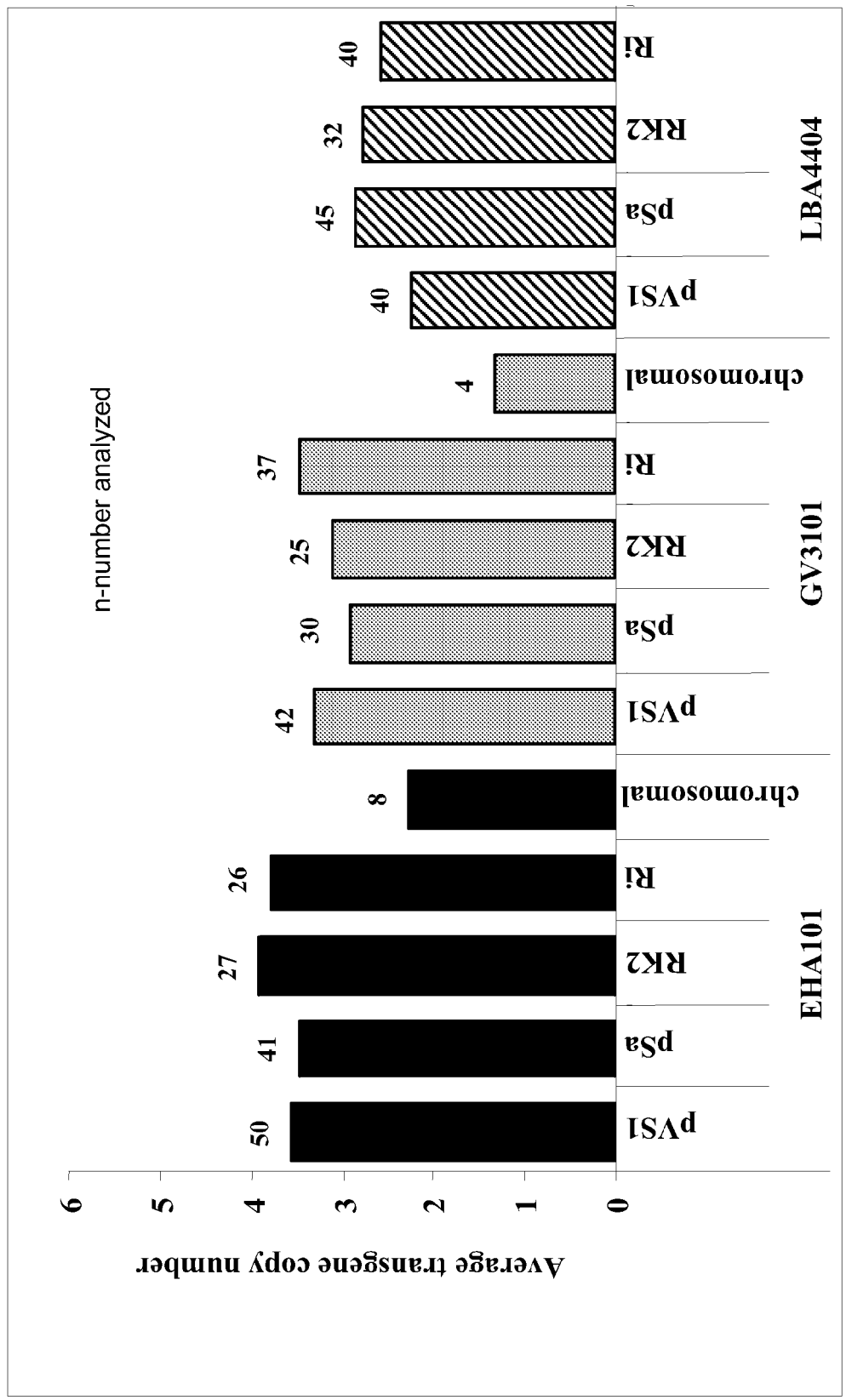

The average transgene copy number for the 14 analyzed strain-by-origin combinations (FIG. 5A) corresponds to the percentage of single transgene integration events. The average transgene copy number for chromosomal integration constructions is low (EHA101: 1.3 copies per diploid genome; GV3101: 1.6 copies per diploid genome), in contrast to the average integrated transgene copy number using T-DNA binary vectors in EHA101 and GV3101 (range 3.3-5.1 transgene copies/diploid genome). The average copy number for the four LBA4044 replication origin combinations is low and lies within a range between 1-2 copies.

Maize T-DNA copy number determinations were made in heterozygous T0 generation plants. Because the bar gene probe used to analyze transgene copy number in *Arabidopsis* resulted in background hybridization signals for wild-type maize DNA, the CaMV double 35S promoter fragment from pTF101.1 was used as a probe (FIG. 1). Copy numbers are also approximated in dot blots shown in FIG. 1A based on the standards. The dot blots were used as a source of data for determining copy number (of each region probed), presence/absence of backbone sequence, and absence of contaminating *Agrobacterium* DNA in the plant DNA preparations. Sequencing of plant DNA preparations or PCRs can also be performed to verify the presence of absence of vector backbone DNA.

Figure 3B:
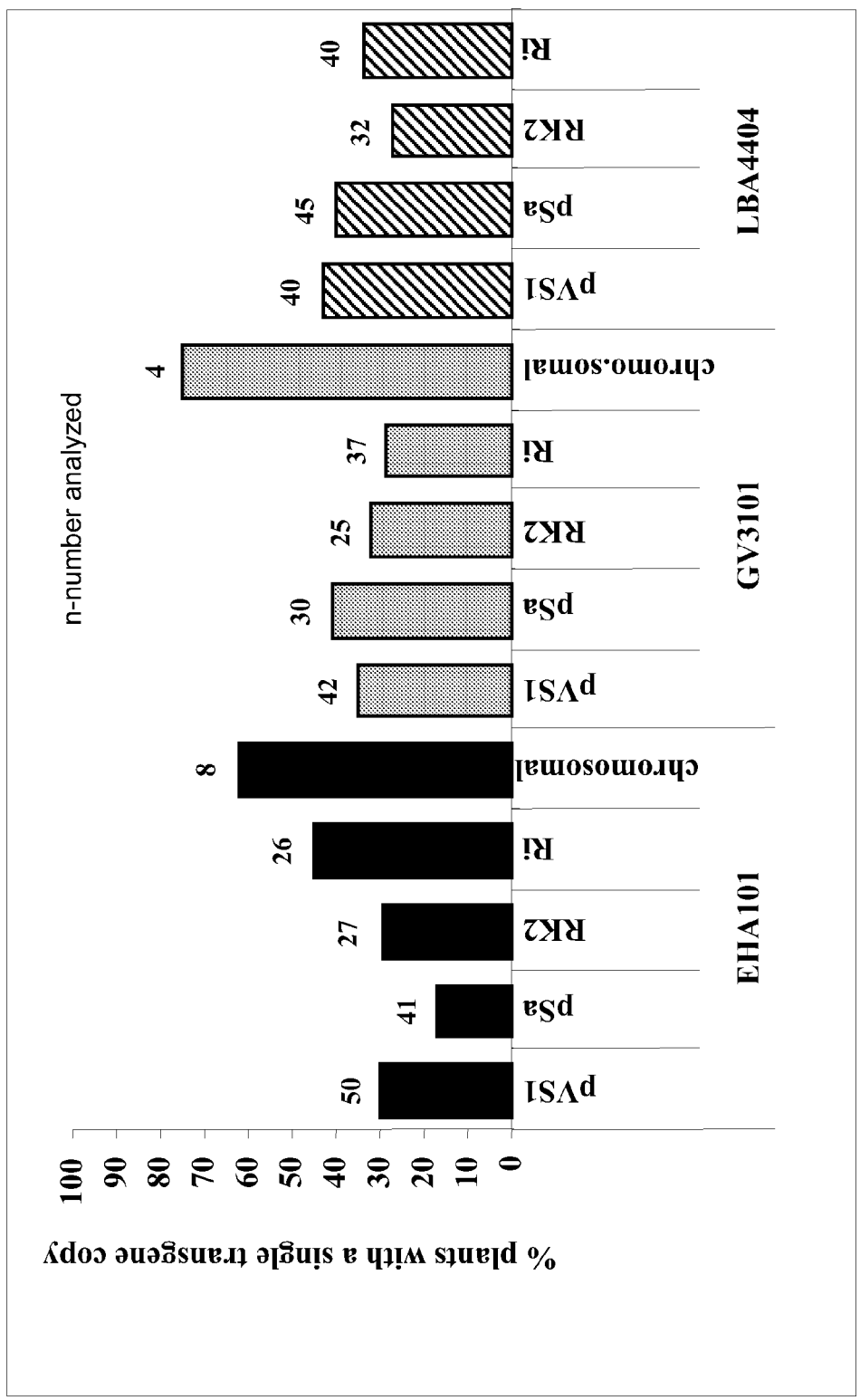

FIG. 3B shows the percentage of maize plants containing a single transgene following transformation using various strain-by-origin combinations. The percentage of plants carrying a single transgene copy varies significantly among the combinations and lies within a range between 22 and 75%. As with *Arabidopsis*, both T-DNA chromosomal integration strain combinations result in a high percentage of single transgene copy number plants: 63% of the plants transformed using the EHA101-by-chromosomal integration combination and 75% of plants transformed using the GV3101-by-chromosomal integration combination harbour a single integrated T-DNA. In contrast, only 17-45% of the plants generated using T-DNA binary vectors contain a single transgene copy.

Although antibiotics were used to kill *Agrobacterium* after transformation, bacterial cells might still contaminate selected transgenic *Arabidopsis* and maize plants. The presence of contaminating *Agrobacterium* DNA would falsely increase the apparent T-DNA copy number. To eliminate this possibility, membranes were hybridized with a fragment containing the picA gene. Hybridization with the picA gene was not detected, indicating that the observed DNA dot blot signals using other probes do not derive from *Agrobacterium* DNA contamination.

Figure 6:
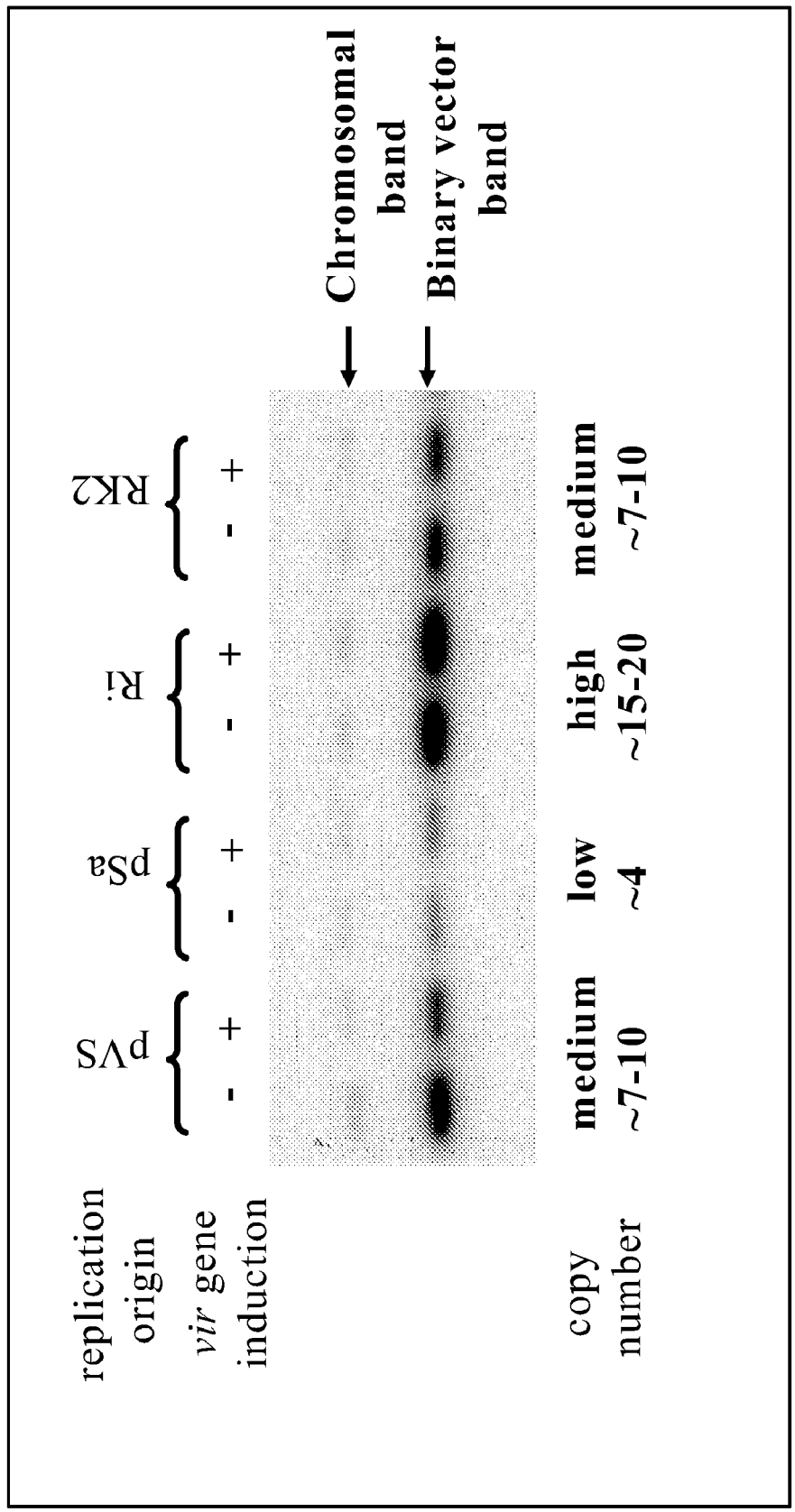
FIG. 6 is a Southern Blot analysis to determine T-DNA vector copy numbers in *Agrobacterium* caused by various replication origins. To estimate the copy number of the T-DNA binary vectors in the bacterial cell, the four T-DNA binary vectors were transformed into an *Agrobacterium* strain which has the bar gene integrated into its chromosome. Total DNA was extracted from *Agrobacterium* cells grown under vir gene inducing and non-inducing conditions and subjected to Southern blot analysis using a bar fragment as a probe. Two bands were visible after exposure: A band for the chromosomal integrated bar gene and a band for the bar gene on the binary vector. Copy numbers were calculated in relation to the chromosomal integration band (which represents 1 copy per cell).

FIG. 6 shows the results of the Southern blot analysis. Copy numbers of the analyzed replication origins vary greatly and are independent of the vir gene induction status. The binary vector copy numbers caused by the pVS, the pSa, and the RK2 replication origins correspond to previous reports in the literature. The pRi copy number (~15-20) is higher than previous findings.

Example 4

Integration of T-DNA into the *Agrobacterium* Chromosome Mitigates Integration of T-DNA Backbone Sequences in Transgenic Plants T-DNA backbone sequences (i.e., sequences not within the defined T-DNA borders) are frequently introduced into plants during *Agrobacterium*-mediated transformation. Such sequences can present regulatory problems, especially when bacterial antibiotic resistance genes are transferred. It was investigated whether the *Agrobacterium* strain or T-DNA replication origin affects the frequency of backbone integration events. All five analyzed T-DNA constructions contain a bacterial spectinomycin resistance (aadA) gene immediately outside the T-DNA left border, to probe all transgenic plant DNA samples for the presence of backbone sequences with an aadA gene fragment (FIG. 1).

FIGS. 4A and 4B show the percentage of transgenic plants with backbone integration events for the 14 strain-by-origin combinations in *Arabidopsis* and maize, respectively. For both *Arabidopsis thaliana* and maize, almost no transgenic plants contained backbone sequences when they were generated by *Agrobacterium* strains in which the T-DNA was integrated into the chromosome, whereas the use of a T-DNA binary vector resulted in a relatively high percentage of plants containing backbone sequences. For *Arabidopsis* only one out of 40 plants that was generated by using the GV3101-by-chromosomal integration combination contained backbone sequences. None of the plants generated by the EHA 101-by-chromosomal integration combination contained vector backbone sequences. In contrast, use of the 12 other combinations harbouring the T-DNA on a binary vector resulted in 47-67% of the plants containing backbone sequences. For maize, backbone sequences were present in only 1 out of 12 plants that were generated using ori-by-strain combinations with a chromosomal integrated T-DNA. The 12 other tested combinations resulted in backbone integration in 19-55% of the resulting transgenic plants.

If T-DNA is processed from a low copy number replicon (such as the chromosome), there are likely to be fewer copies processed in *Agrobacterium*. When *Agrobacterium* is in a plant environment to transfer, the Ti-plasmid over-replicates 5-10 fold with respect to the chromosome and data indicate that up to 14 copies of T-DNA can be processed (repeatedly) from the same Ti-plasmid. Based on this, when a high copy number binary vector is used, it is expected that a large number of T-strands are processed to be transferred. In the case of chromosomal integration of T-DNA, because the T-DNA is integrated into a very large replicon (the chromosome), for example, if the left border (LB) is "skipped", this may result in a long stretch of transfer DNA (because in a chromosome it may take a long distance to stop at a sequence that resembles the border sequence, i.e., pseudoborder). Such a long T-strand may not be able to exit the bacterium efficiently and therefore may not transverse the plant cytoplasm and may not integrate into the plant chromosome. Therefore, launching of T-DNA from *Agrobacterium* chromosome may screen out integration of vector backbone sequences into plant genome.

Example 5

Construction of Chromosomal Integration Vectors and Integrating a Gene of Interest into *Agrobacterium* Chromosome A chromosomal insertion site of a genetic element (e.g., a gene) generally may not affect either bacterial virulence or growth rate of *Agrobacterium*. A plant-inducible locus on the *Agrobacterium* chromosome (pica) is not required either for bacterial growth or T-DNA transfer. The pica and neighboring pgl (polygalacturonase like) genes are located on a 3.15-kbp EcoRI fragment of the chromosome of *A. tumefaciens* C58. A PstI site exists between these two genes. Insertion of a gene into this PstI site leaves enough length of DNA sequence on both sides (1.3 kb and 1.8 kb, respectively) to allow efficient double homologous recombination into the bacterial chromosome. This EcoRI fragment was cloned onto an IncPα plasmid, pLAFR1, to make a basic integration vector pE578. In order to facilitate integration of the GOI into the *Agrobacterium* chromosome, the basic vector was modified and several features were added.

Figure 1B:
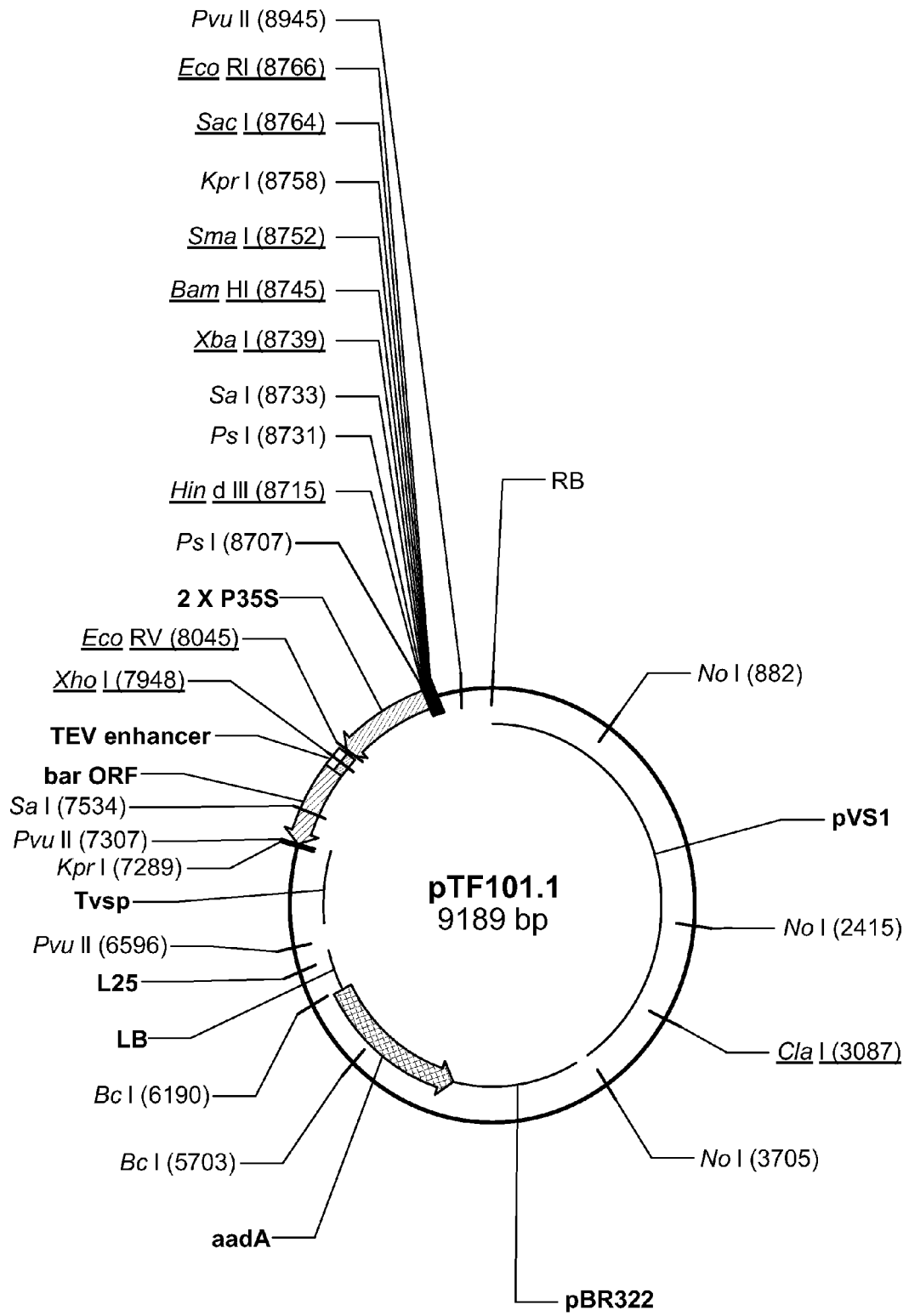
FIG. 1B is a map of one of the binary vectors used in *Agrobacterium* transformation.
Figure 1C:
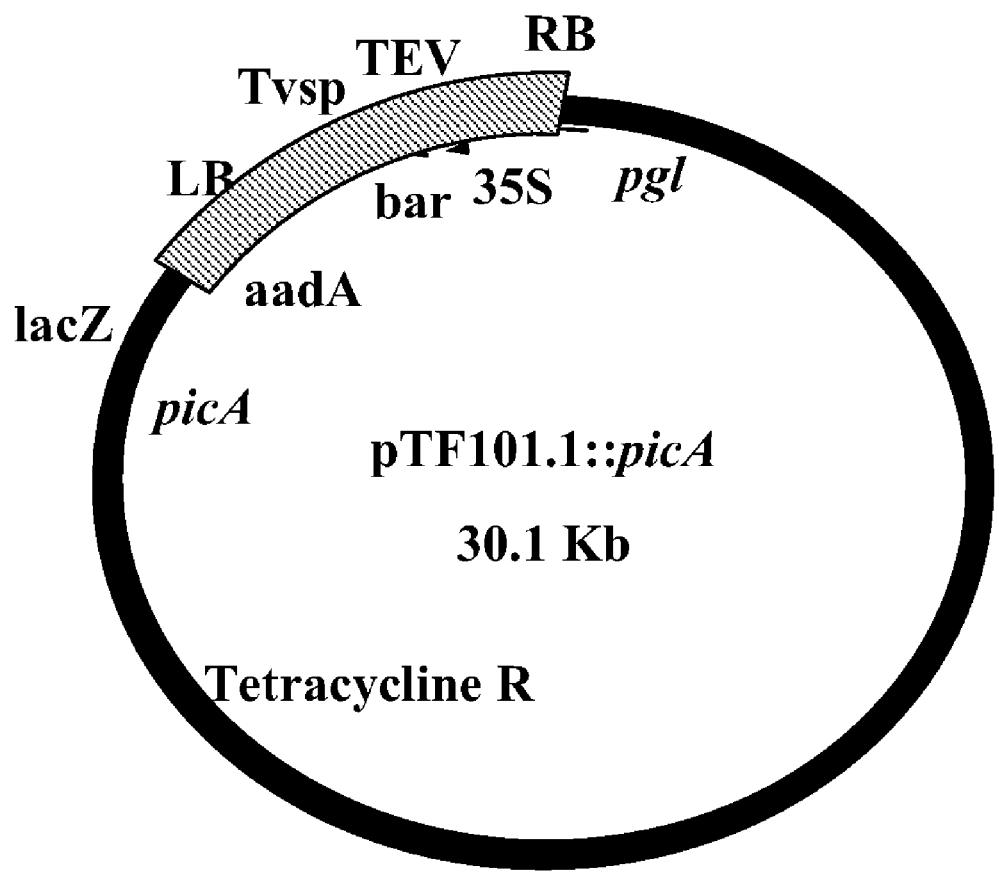
FIG. 1C is an example of a chromosomal integration vector.
Figure 1D:
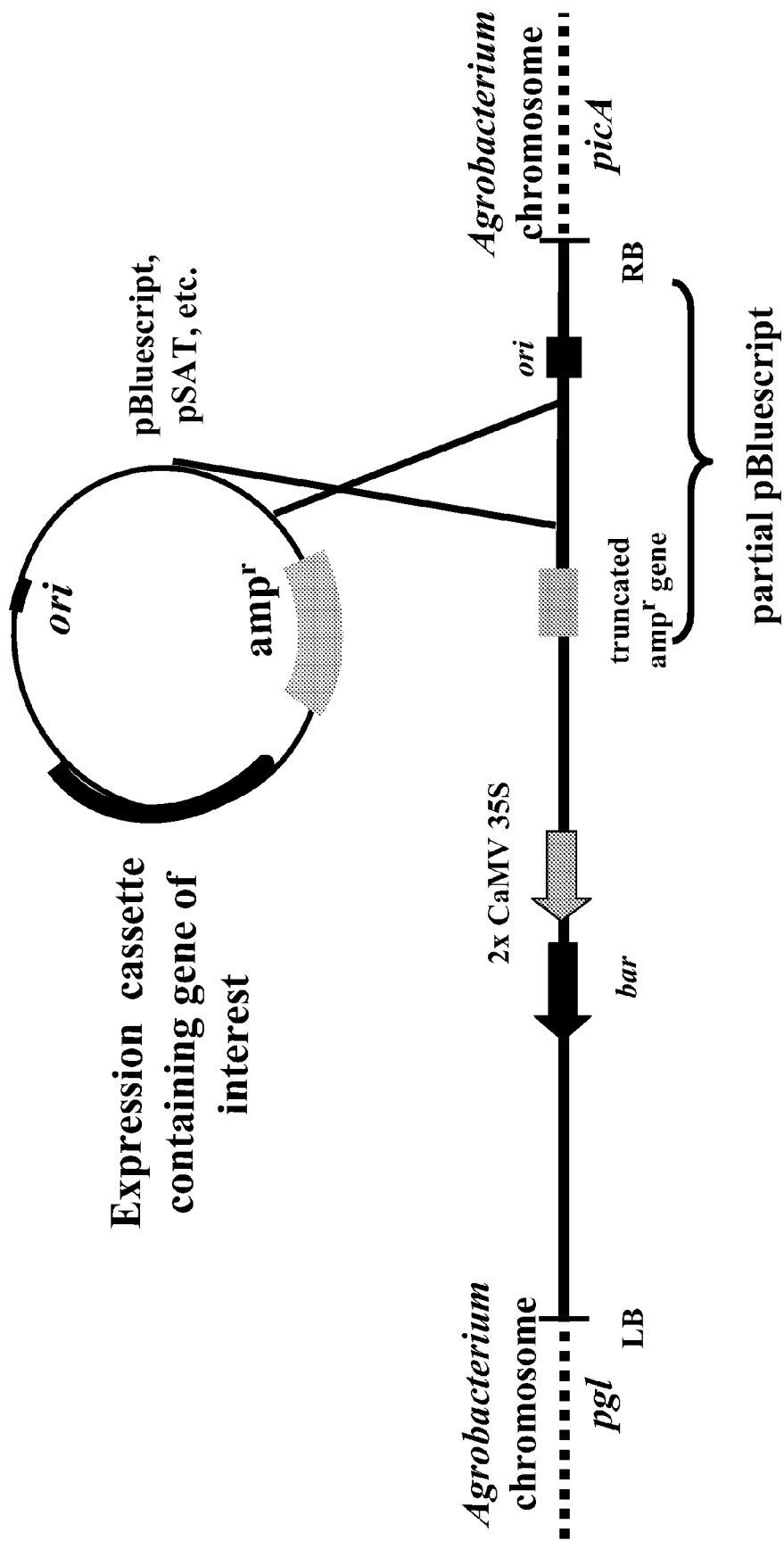
FIG. 1D shows development of an *Agrobacterium* strain to facilitate launching T-DNA from the *Agrobacterium* chromosome.

FIG. 1B-D show examples of illustrations of chromosomal integration vectors and generation of launching pads for T-DNA integration into plant genomes.

Figure 8:
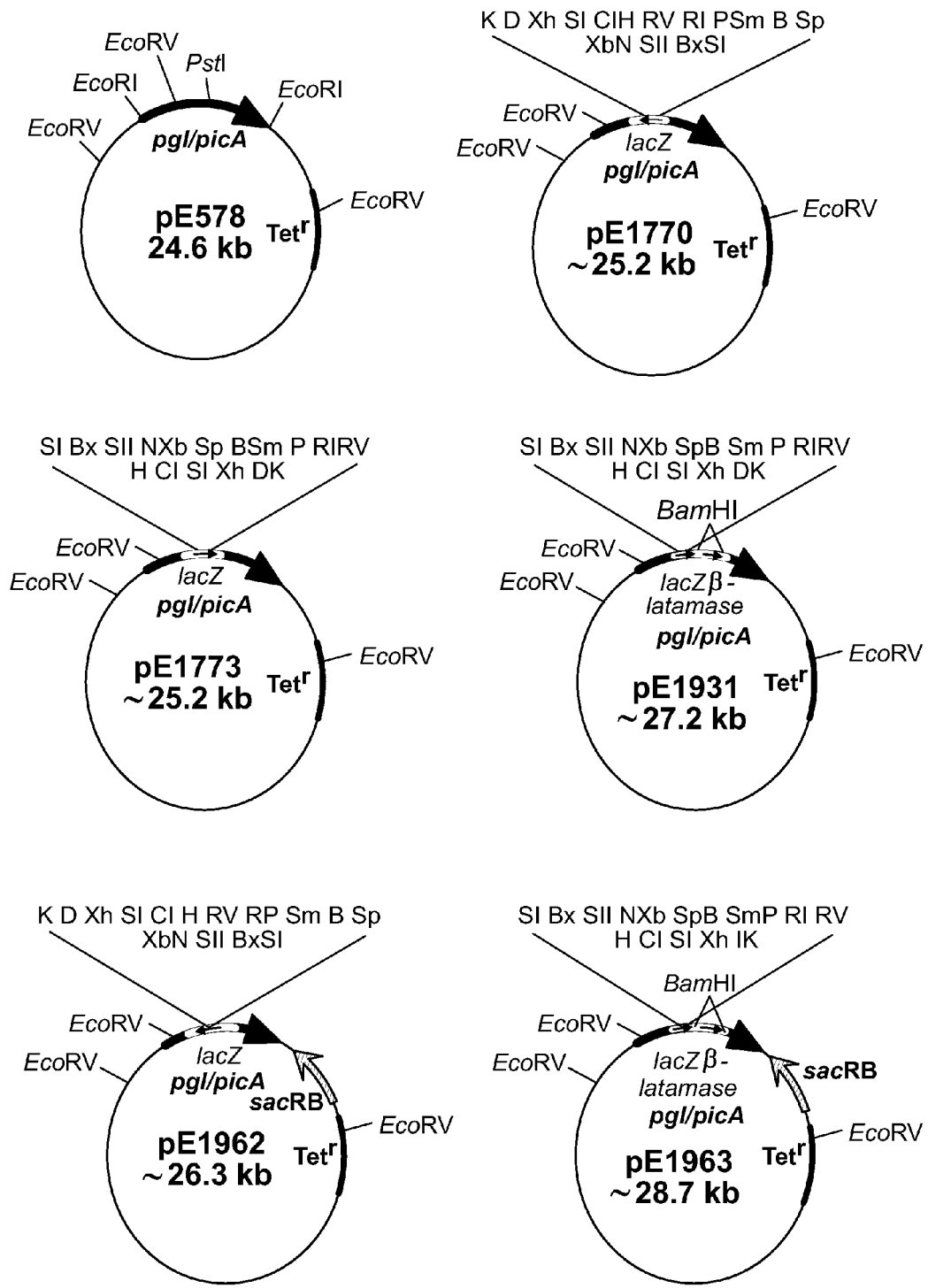
FIG. 8 illustrates several maps of the *Agrobacterium* integration vectors described herein. The plasmids are not necessary drawn to scale. Restriction enzyme sites in bold are unique on the plasmids. B, BamHI; Bg, BglII; Bx, BstXI; Cl, ClaI; D, DraI; H, HindIII; K, KpnI; N, NotI; P, PstI; RI, EcoRI; RV, EcoRV; SI, SacI; SII, SacII; SI, SalI; Sm, SmaI; Sp, SpeI; Xb, XbaI; Xh, XhoI.

Groups of vectors (e.g., plasmids pE1770 and pE1773) may contain a lacZ α-complementation fragment that has unique restriction enzyme sites (KpnI, HindIII, EcoRI, PstI, BamHI, SpeI, XbaI, and Sac) between the picA and pgl genes and examples are shown in FIG. 8. Using blue-white colony screening these sites are used to clone a gene of interest (GOI) and a selectable antibiotic resistance marker into these sites. The antibiotic resistance marker is used as an indicator of gene replacement in subsequent steps of the procedure. Alternatively, the GOI is cloned into a cloning vector containing a ColEI replication ori (such as pUC or pBluescript) first, and then cointegrate the entire plasmid into one of the unique restriction enzyme sites in the lacZ α-complementation fragment. The β-lactamase (ampicillin/carbenicillin resistance) gene on the backbone of this cloning plasmid can also be used as a selection marker to determine whether the GOI has integrated onto the *Agrobacterium* chromosome.

A β-lactamase gene can also be inserted into the pgl/picA locus to allow for the introduction of GOI (e.g., pE1931 and pE1963, FIG. 8). The sacR and sacB genes from *Bacillus subtilis* can also be included on the plasmid backbones instead of a β-lactamase gene (e.g., pE1962 and pE1963, FIG. 8). Because the sacB gene product metabolizes sucrose to a toxic compound, sucrose containing medium is used to select for double crossover recombinants (and the loss of the sacB containing vector) at the pgl/picA locus of *A. tumefaciens* C58. Blue-white colony screening can also be used to clone GOI into the plasmids.

Figure 7:
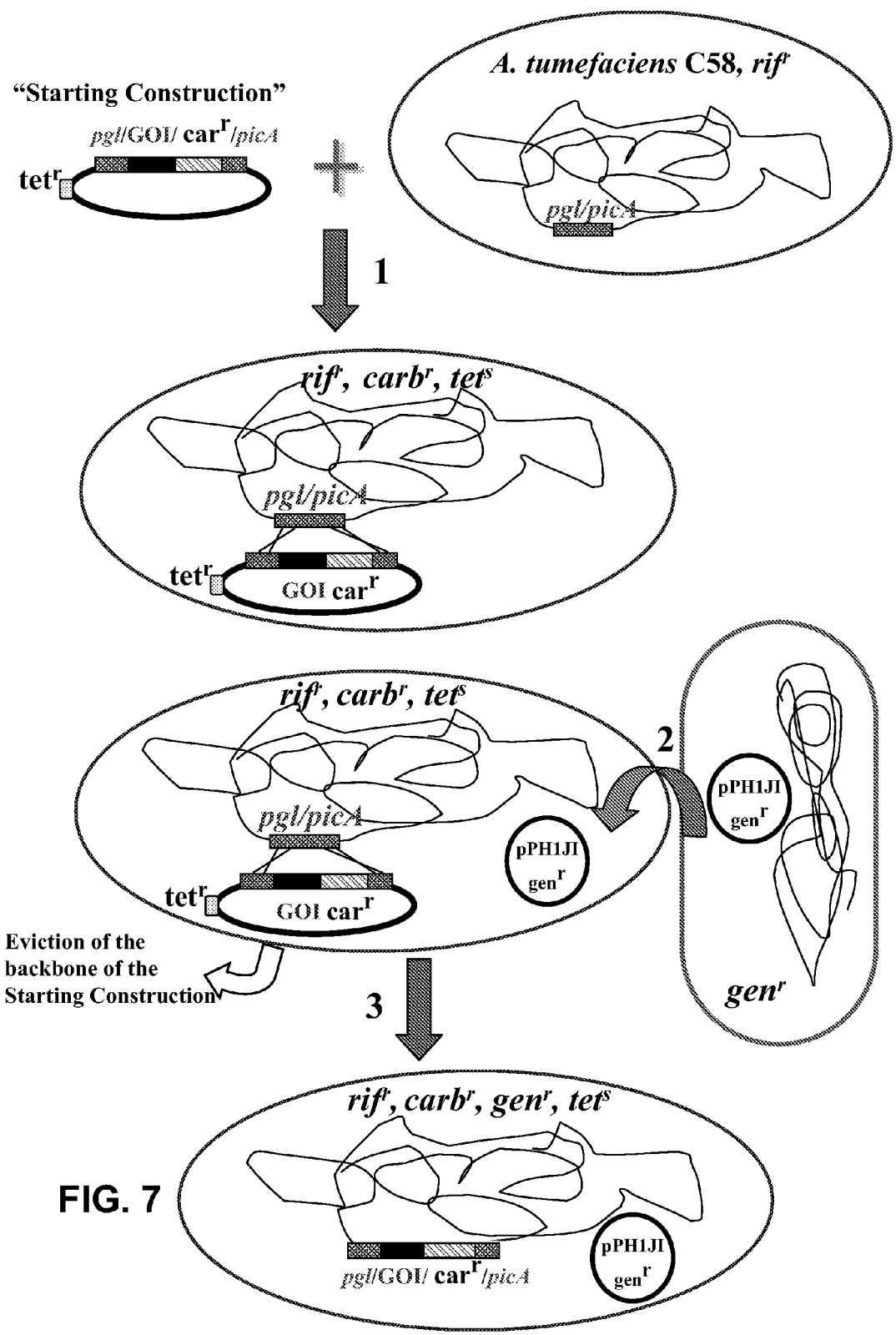
FIG. 7 is a schematic representation of the experimental design for placing a gene of interest into the pgl/picA region of the *A. tumefaciens* C58. Step 1: Introduction of the Starting Construction into *A. tumefaciens* C58 using bacterial mating or transformation. Step 2: Introduction of an eviction plasmid by bacterial conjugation. Step 3: Selection of the final transconjugants. GOI, gene of interest; car$^r$, carbenicillin resistance gene; gent, gentamicin resistance gene; tetr, tetracycline resistance gene.
Figure 9:
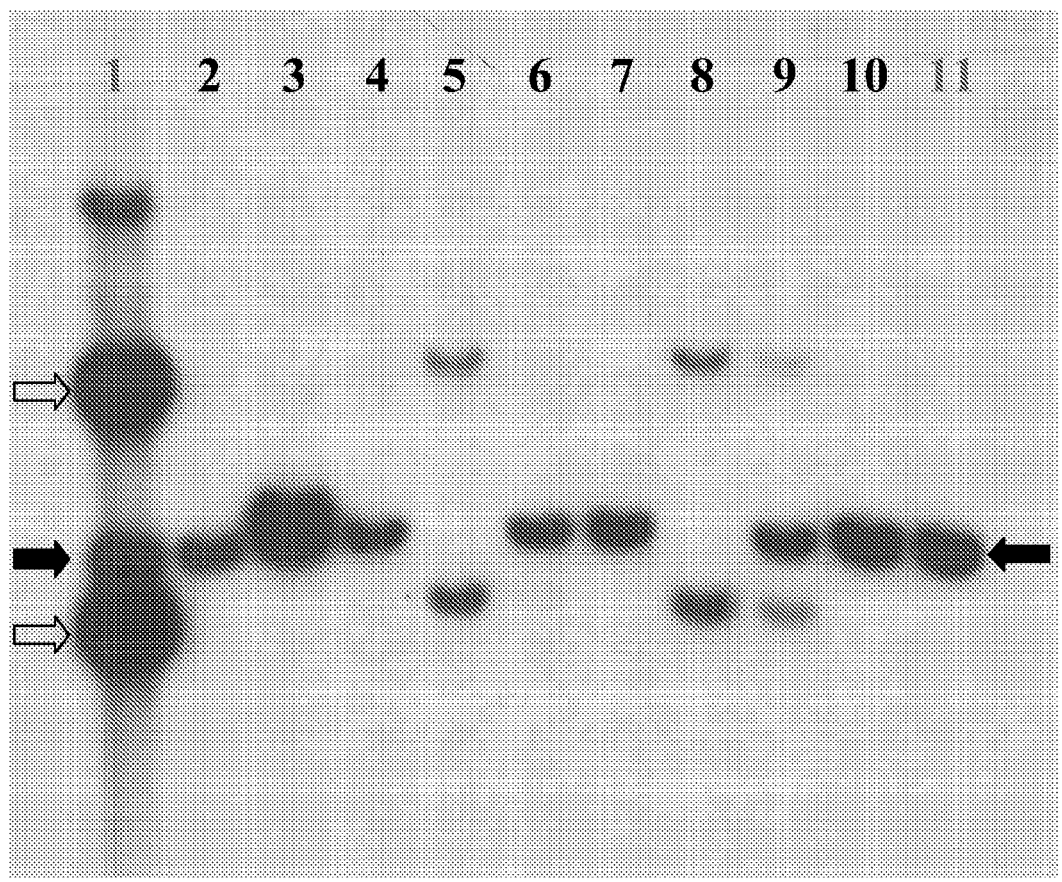
FIG. 9 shows an example of a Southern hybridization to verify the integration of the gene of interest into the chromosomal pgl/picA locus of *A. tumefaciens*.

To perform the chromosomal integration (FIG. 7), the GOI is placed between the pgl and picA genes on any suitable vector to make the "Starting Construction". Next, the Starting Construction is introduced into *A. tumefaciens* C58 (or any suitable strain) either by bacterial conjugation (triparental mating), transformation, or electroporation to make the "Starting Strain". An eviction plasmid belonging to the IncPα group, such as pPH1JI (Hirsh, 1984) or pVK102 (Knauf, 1982), is then introduced into the Starting Strain by bacterial mating. Transconjugants which are resistant to both the antibiotic marker introduced near the GOI and the antibiotic resistance marker on the backbone of the eviction plasmid (gentamicin resistance for pPH1JI or kanamycin resistance for pVK102) are selected. Because the integration vectors and the eviction plasmids belong to the same IncPα incompatibility group, they cannot co-reside as replicons in the same bacterial cell. These transconjugants, which are resistant to both antibiotics, will fall into two possible categories. The first category are bacteria that contain the entire starting plasmid integrated into the chromosome DNA through a single crossover recombination event (a plasmid co-integrate). The second category are bacteria with the GOI and selection marker exchanged into the pgl/picA locus through double homologous recombination. Whether these transconjugants are resistant to the antibiotic encoded by the resistance marker on the backbone of the Starting Construction (for these plasmids, tetracycline) can be checked. If the transconjugant is resistant to tetracycline, this indicates that the strain has the entire Starting Construction integrated into the chromosome. This type of transconjugant is generally discarded. Only those transconjugants which are sensitive to tetracycline are kept. Finally, one needs to extract total genomic DNA from these transconjugants. Following digestion with the appropriate restriction enzymes and Southern blot analysis, one can determine whether the GOI and antibiotic resistance markers have been exchanged into the pgl/picA locus on the chromosome (FIG. 9).

DNA from *A. tumefaciens* strains was digested with EcoRI and blotted onto a nylon membrane. A labeled 3.15-kbp DNA probe containing the pgl/picA locus was used to confirm the disruption of the pgl/picA locus in various *A. tumefaciens* strains. In FIG. 9, Lane 1 corresponds to the *A. tumefaciens* strain C58 containing the Starting Construction. Lane 2-10 are 9 individual clones which may or may not have the integration of the GOI. Lane 11 is *A. tumefaciens* strain C58. Solid black indicates the intact 3.15-kbp pgl/picA locus from the wild type *A. tumefaciens* chromosome (Lane 1 and Lane 11). Line arrow indicates DNA fragments from the disrupted pgl/picA locus on the Starting Construction (Lane 1). Note that the intensity of the DNA band from the chromosome (single copy) is lower than that of the disrupted locus from the multiple copy plasmid. Results from the genomic DNA samples of Lane 5 and Lane 8 indicate that these two *A. tumefaciens* strains contain the GOI integrated in the chromosomal region (note that the intensity of the DNA bands is similar to that of the chromosomal locus). However, results from Lane 2-4, Lane 6-7 and Lane 10 suggest these *A. tumefaciens* strains do not have the GOI integrated (same pattern as Lane 11). Interestingly, Lane 9 shows that the *A. tumefaciens* strain has both a wild-type and a disrupted copy of the pgl/picA locus, indicating that this strain carries the entire Starting construction as a co-integrate in its chromosome.

The GOI is stably maintained in this *Agrobacterium* strain at a single copy per cell without applying selection pressure.

Methods

*Agrobacterium tumefaciens* Strains

*Agrobacterium tumefaciens* strains were grown either on solidified AB sucrose medium (Lichtenstein and Draper, (1986), In Genetic Engineering of Plants, Vol. 2 (Glover, D. M., ed.). Washington, D.C.: IRL Press, pp. 67-119) or in yeast extract peptone medium supplemented with appropriate antibiotics (rifampicin, 10 µg/ml; spectinomycin, 100 µg/ml; kanamycin, 25 µg/ml; gentamicin, 25 µg/ml).

T-DNA Constructions

The T-DNA region and the bacterial aadA (spectinomycin resistance) gene (FIG. 1) used in all T-DNA binary constructions derives from pTF101.1, whose DNA sequence is described herein. pTF101.1 contains a pVS1 origin of replication. To generate the various binary vectors, the pVS1 replication origin (ori) was replaced with those from other plasmids. For introducing the RK2 ori, the pVS1 origin was removed from pTF101.1 using ScaI and NotI and replaced it with a NotI/NruI fragment from pBIN19, generating pTF::Bin19. For introducing the pSa ori, the pVS1 ori was removed from pTF101.1 using ScaI and NsiI and replaced it with a PstI/SacII fragment from pUCD2. All overhanging ends were made blunt using T4 DNA polymerase (New England Biolabs, Ipswich, Mass., USA) to enable ligation. The resulting plasmid was designated pTF::UCD2. The pRiA4b origin was amplified from *A. rhizogenes* strain A4 (Jouanin et al., (1986), *Plasmid* 16:124-134) using PCR primers. The amplified PCR fragment was cloned into pBluescript SK+ (Stratagene, La Jolla, Calif.) and designated pBluescript::Ri. To confirm that the cloned pRi replication origin effects replication in *Agrobacterium*, pBluescript::Ri was transformed into *A. tumefaciens* by electroporation (Nagel et al., (1990), *FEMS Microbiol. Lett.* 67:325-328) and plasmid DNA was isolated from carbenicillin-resistant colonies. pBluescript::pRi was digested with ClaI and the overhanging ends were made blunt using T4 DNA polymerase. The product was subsequently digested with NotI and cloned into pTF101.1 prior digested with ScaI and NotI to remove the pVS1 replication origin. The resulting plasmid was designated pTF::Ri.

The four T-DNA vectors pTF101.1, pTF::Bin19, pTF::UCD2 and pTF::Ri were separately transformed into *A. tumefaciens* EHA101 (Hood et al., 1987), GV3101 (Koncz and Schell, 1986), and LBA4404 (Ooms et al., 1981) by electroporation (Nagel et al., 1990).

The T-DNA region plus the aadA gene of pTF101.1 (a 4.2 kb ScaI-NsiI fragment) was inserted into the blunted SpeI site and PstI site of the integration vector pE1931. This plasmid (pE2759) was separately introduced into *A. tumefaciens* EHA101 and GV3101. The eviction plasmid pPH1JI was introduced into the resulting strains, and colonies were selected on gentamicin and carbenicillin. Tetracycline-sensitive colonies (which had lost pE2759) were selected, and recombination of the T-DNA region into the pgl/picA locus of the *Agrobacterium* chromosome was confirmed by DNA blot hybridization (Lee et al., 2001).

Agrobacterium-Mediated Transformation of *Arabidopsis thaliana* and Maize

All 14 *Agrobacterium* strain-by-replication origin combinations were utilized to transform *Arabidopsis thaliana* and maize. *Arabidopsis thaliana* (ecotype Wassilewskija, Ws2) was transformed by a floral dip protocol (Clough and Bent, 1998). Phosphinothricin resistant plants were selected on Gamborg's B5 Medium (Caisson Laboratories, Rexburg, Id.) supplemented with 10 µg/ml phosphinothricin and 100 µg/ml timentin. Transformation frequencies were calculated as follows: [Number of phosphinothricin resistant plants/number of seeds tested]×100. 10 mg of seeds correspond to approximately 500 seeds.

Maize was transformed by infecting immature zygotic embryos (1.2-1.5 mm) of the Hi II genotype with bacterial suspensions ($A_{550}$=0.3-0.4) initiated from solid cultures grown for 3 days (19° C.) on YEP medium containing rifampicin and spectinomycin). Infected embryos were co-cultivated for 3 days (20° C., dark) on N6 Medium (Phytotechnology Labs, Shawnee Mission KS) containing 300 mg/L L-cysteine. Selection for bialaphos resistant callus events and regeneration of transgenic plants was accomplished as described in Frame et al., 2002, incorporated herein by reference (*Plant Physiol.* 129: 13-22).

Genomic DNA Extraction and DNA Dot Blot Preparation

Genomic DNA was extracted from 3-5 leaves of 3-4 week old *Arabidopsis thaliana* plants or approximately 100 mg maize leaf tissue (Murray and Thompson (1980), *Nucl. Acids Res.* 8:4321 4325). Genomic DNA was quantified using a Gemini XPS microplate spectrofluorometer (Molecular Devices, Sunnyvale, Calif., USA, excitation: 488 nm emission: 525 nm) and the Quant-iT™ PicoGreen® dsDNA Assay Kit (Invitrogen Inc.; Carlsbad, Calif., USA).

DNA dot blots were prepared to determine T-DNA copy numbers and the frequency of T-DNA backbone integration events. *Arabidopsis* (75 ng) or maize (1.5 µg) genomic DNA samples were denatured by adding NaOH and EDTA to a final concentration of 0.4 M and 10 mM, respectively, followed by 10 min incubation in boiling water. A Hybond N+nylon membrane (Amersham Pharmacia Biotech, Piscataway, N.J., USA) was pre-wetted with water and placed between the layers of the dot blot apparatus. Samples were applied to the wells of the dot blot apparatus, incubated for 30 min, and then drawn onto the nylon membrane using a gentle vacuum. DNA was cross-linked to the membrane by using a CL-1000 UV crosslinker (UVP, Upland, Calif.). The membranes were incubated in 2×SSC for 10 min and dried.

DNA Dot Blot Hybridization

Probes for dot blot hybridizations were generated using random prime Ready-To-Go DNA Labelling Beads and $^{32}$P-dCTP (both Amersham Pharmaca Biosciences). Unincorporated radioactive nucleotides were removed by Sephadex G-100 gel filtration. Membranes were pre-hybridized in 7% (w/v) SDS, 0.5 M sodium phosphate (pH 7.2) and 10 mM EDTA (pH 8.0) at 65° C. for two hours. Hybridization was done overnight at 65° C. After hybridization membranes were washed 2 times with 2×SSC, 0.1% (w/v) SDS, 10 mM EDTA (pH 8.0), then 2 times with 1×SSC, 0.1% (w/v) SDS, 10 mM EDTA and finally 2 times with 0.1×SSC, 0.1% (w/v) SDS, 10 mM EDTA at 65° C. Membranes were exposed at –80° C. for autoradiography. Integrated dot density was determined using Labworks 4.6 Image Acquisition and Analysis Software (UVP, Upland, Calif.). For re-probing, membranes were stripped using boiling 0.1% (w/v) SDS twice.

DNA dot blot membranes were hybridized subsequently with various probes. For determining T-DNA copy numbers of *Arabidopsis* plants, dot blot membranes were hybridized with a 559 bp bar PCR fragment (FIG. 1). The PCR fragment was amplified using pTF101.1 as template and 5'-GAT CTA CCA TGA GCC CAG AAC G-3' (SEQ ID NO: 1) and 5'-CAG ATC TCG GTG ACG GGC AGG A-3'(SEQ ID NO: 2) as primers. In order to determine T-DNA copy numbers of maize plants, membranes were probed with a 759 bp PstI/XhoI fragment from pTF101.1 harbouring the double CaMV 35S promoter (FIG. 1). To detect vector backbone sequences in both *Arabidopsis* and maize DNA, a 656 bp PCR fragment derived from the non-T-DNA region next to the T-DNA left border of pTF101.1 (FIG. 1) was used as a probe. The fragment was amplified using pTF101.1 as a template and 5'-TCA CCG TAA CCA GC AAA TCA-3' (SEQ ID NO: 3) and 5'-CTC GGC ACA AAA TCA CCA CT-3' (SEQ ID NO: 4) as primers. A 3.1 kb EcoR1 fragment containing the pgl/picA locus (Rong et al., (1990), *J. Bacteriol.* 173, 5110-5120) was used as a probe to check for the presence of contaminating *Agrobacterium* DNA in plant genomic DNA. All DNA fragments were gel purified prior to labelling using a QIAEX II Gel Extraction Kit (QIAGEN, Hilden, Germany). In order to normalize amounts of DNA in each dot, membranes were hybridized with genomic *Arabidopsis* or maize DNA.

Subcloning the GOI into the Integration Vector

1 Choose the appropriate restriction enzyme sites to use for insertion of the GOI into the integration vector.
2. Cut out the insert with appropriate restriction enzyme(s); elute the insert fragment from a gel if it is necessary. Follow the manufacturer's instructions.
3. Ligate the insert DNA to vector DNA and transform an *E. coli* host to obtain the Starting Construction.
4. Select and analyze the *E. coli* transformants. The *E. coli* colony with the correct Starting Construction will be used for the following experiment.

Introduction of Starting Construction into *Agrobacterium*:
Triparental Mating (Conjugation):

1. Grow 5 ml liquid cultures of each bacterial strain overnight: *A. tumefaciens* containing the C58 chromosomal background (resistant to rifampicin), *E. coli* strain E9 (resistant to gentamicin), and the *E. coli* strain containing the Starting Construction (let's assume this strain is resistant to both ampicillin from the selectable marker near the GOI, and tetracycline from the backbone of the integration vector) obtained herein.
2. The next day, transfer 1 ml of each bacterial culture into an individual 1.5-ml microfuge tube. Centrifuge the cell pellets using the maximum microcentrifuge speed for one minute.
3. Wash the cell pellets once with sterile 0.9% NaCl and resuspend the cells in 1 ml 0.9% NaCl.
4. Mix 0.2 ml of each bacterial solution in a 1.5-ml microfuge tube. Take 10 µl of the bacterial mixture and spot on a LB agar plate.
5. Incubate the plate at 30° C. overnight.
6. The next day, use 1 ml of sterile 0.9% NaCl to wash most of the bacteria from the mating plate. This is the undiluted bacterial conjugation mixture. Make 10-fold serial dilution of this conjugation mixture with sterile 0.9% NaCl. Plate out 100 µl of diluted ($10^{-3}$ and $10^{-4}$ dilutions) conjugation mixture onto the selection medium containing the appropriate antibiotics (AB-Sucrose medium containing rifampicin and carbenicillin).
7. Incubate the plates at 30° C. for 2-4 days. Colonies appearing on these selection plates are potential transconjugants.

Confirmation of *Agrobacterium* Cells that have Received the Starting Construction 8. Re-streak several potential transconjugants grown on an AB-Sucrose agar plate containing tetracycline to check antibiotic sensitivity. Pick one of the transconjugants that is resistant to tetracycline and continue the following experiment.

Eviction of the Starting Construction from *Agrobacterium*

1. Inoculate a single colony of the *A. tumefaciens* strain into 5-ml YEP liquid medium containing carbenicillin. Also inoculate a single colony of *E. coli* strain E4 in 5-ml LB liquid medium containing gentamicin.
2. Grow both cultures at 30° C. overnight with shaking.
3. The next day, wash 1 ml of each culture once with sterile 0.9% NaCl in a sterile microcentrifuge tube, then resuspend the cell pellets in 1 ml of 0.9% NaCl.
4. Mix 0.2 ml of *Agrobacterium* cells with 0.2 ml of *E. coli* strain E4 in a tube. Take out 10 µl of mixture and spot on a LB agar plate.
5. Incubate the plate at 30° C. overnight. The next day, use 1 ml of sterile 0.9% NaCl to suspend the conjugation mixture. Make 10-fold serial dilutions in 0.9% NaCl and plate 100 µl of each dilution ($10^{-2}$, $10^{-3}$, and $10^{-4}$ dilutions) on selection medium (AB-Sucrose agar medium containing carbenicillin and gentamicin) to screen for cells which have the GOI and selection marker integrated onto the chromosomal pgl/picA locus through homologous recombination.
6. Incubate the plate at 30° C. for 2-3 days. Colonies appearing on selection medium potentially contain the GOI integrated into the *Agrobacterium* chromosome.
7. Streak several colonies from the previous step on plates containing AB-Sucrose agar medium with either carbenicillin and gentamicin, or tetracycline, respectively. Only keep the strains which are resistant to both carbenicillin and gentamicin and are sensitive to tetracycline.
8. *E. coli* strain E618 can be used when an *Agrobacterium* strain is already resistant to gentamicin. This strain contains pVK102, which carries kanamycin and tetracycline resistance genes.
9. If both a GOI and a selectable marker are placed into the integration vector to make the Starting Construction, pE1770 or pE1773 can be used. If a GOI needs to be placed into an integration vector that already contains a selectable marker, pE1931 or pE1963 can be used. If the sucrose counter-selection method, pE1963 or pE1962 can be used (FIG. 8). Alternatively, plasmid DNA from the *Agrobacterium* transconjugant can be extracted and *E. coli* can be re-transformed with this plasmid DNA. If the new *E. coli* transformants are now resistant to both markers (in this case, they are ampicillin and tetracycline) from the Starting Construction, this suggests that this *Agrobacterium* transconjugant does contain the Starting Construction.
10. Dissolving bacterial genomic DNA takes longer at a higher concentration. The tube containing the DNA may be incubated at 37° C. for about 30 minutes to dissolve the DNA. Alternatively, more TE buffer can be used to dissolve the DNA. Vortexing the DNA is not recommended as it will shear the DNA.

The invention claimed is:

1. A method of reducing transgene copy number and minimizing integration of vector backbone sequence in a transgenic plant, the method comprising:
   (a) obtaining an *Agrobacterium* strain comprising a T-DNA sequence integrated into an *Agrobacterium* chromosome, wherein the T-DNA sequence comprises a DNA sequence of interest flanked by T-DNA border repeat sequences and wherein the T-DNA is integrated into a locus in the *Agrobacterium* chromosome that does not significantly affect the growth or virulence of the *Agrobacterium*;
   (b) transforming a suitable host plant material with the *Agrobacterium*; and
   (c) testing whether transgene copy number and vector backbone sequences are minimized in the resulting transgenic plant.

2. The method of claim 1, wherein the *Agrobacterium* strain is selected from the group consisting of EHA101, EHA105, GV3101, and LBA4404.

3. The method of claim 1, wherein host plant material is from a monocot.

4. The method of claim 1, wherein the locus is picA/pgl.

5. A method to generate a transgenic plant with a single transgenic copy of a DNA sequence of interest, the method comprising:
   (a) obtaining an *Agrobacterium* strain comprising a T-DNA sequence integrated into the *Agrobacterium* chromosome, wherein the T-DNA sequence comprises the DNA sequence of interest and wherein the T-DNA is integrated into a locus in the *Agrobacterium* chromosome that does not significantly affect the growth or virulence of the *Agrobacterium*;
   (b) transforming a suitable host plant material with the *Agrobacterium*;
   (c) determining the copy number of the gene of interest in the transgenic plant; and
   (d) selecting the transgenic plant with a single copy of the DNA sequence of interest.

6. The method of claim 5, wherein the transgenic plant is without a vector backbone sequence.

7. An *Agrobacterium* strain comprising a T-DNA integrated into a chromosomal locus of the *Agrobacterium*, wherein the T-DNA comprises a DNA sequence of interest and a selectable marker and wherein the T-DNA is capable of being integrated stably as a single copy in a plant genome and delivered into a plant cell without any vector backbone sequence, and wherein the T-DNA is integrated into a locus in the *Agrobacterium* chromosome that does not significantly affect the growth or virulence of the *Agrobacterium*, wherein the chromosomal locus is picA/pgl.

8. The *Agrobacterium* strain of claim 7, wherein the T-DNA is flanked by a portion of the *Agrobacterium* chromosome to facilitate homologous recombination.

9. The *Agrobacterium* strain of claim 7 wherein the DNA sequence of interest comprises a plant-expressible promoter operably linked to a heterologous coding sequence.

* * * * *

UNITED STATES PATENT AND TRADEMARK OFFICE
CERTIFICATE OF CORRECTION

| | | |
|---|---|---|
| PATENT NO. | : 8,334,428 B2 | Page 1 of 1 |
| APPLICATION NO. | : 12/514180 | |
| DATED | : December 18, 2012 | |
| INVENTOR(S) | : Stanton B. Gelvin | |

It is certified that error appears in the above-identified patent and that said Letters Patent is hereby corrected as shown below:

In the Specifications:

In Column 1, the paragraph beginning at line 12 should read as follows:

--This invention was made with government support under grant number 501-1392-0542 awarded by the NSF Fund No NTP0542. The government has certain rights in the invention.--

Signed and Sealed this
Second Day of April, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,334,428 B2 | Page 1 of 1 |
| APPLICATION NO. | : 12/514180 | |
| DATED | : December 18, 2012 | |
| INVENTOR(S) | : Stanton B. Gelvin | |

It is certified that error appears in the above-identified patent and that said Letters Patent is hereby corrected as shown below:

In the Specifications:

In Column 1, the paragraph beginning at line 12 should read as follows:

--This invention was made with government support under grant number DBI-0110023 awarded by the NSF. The government has certain rights in the invention.--

This certificate supersedes the Certificate of Correction issued April 2, 2013.

Signed and Sealed this
Twenty-first Day of May, 2013

Teresa Stanek Rea
*Acting Director of the United States Patent and Trademark Office*